United States Patent
Nakai et al.

(10) Patent No.: US 8,401,267 B2
(45) Date of Patent: Mar. 19, 2013

(54) MEDICAL X-RAY CT IMAGING APPARATUS

(75) Inventors: Teruji Nakai, Kyoto (JP); Kouji Yasuda, Kyoto (JP); Tetsuzo Ito, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 254 days.

(21) Appl. No.: 12/736,664

(22) PCT Filed: Apr. 28, 2009

(86) PCT No.: PCT/JP2009/058374
§ 371 (c)(1),
(2), (4) Date: Oct. 28, 2010

(87) PCT Pub. No.: WO2009/133896
PCT Pub. Date: Nov. 5, 2009

(65) Prior Publication Data
US 2011/0044520 A1     Feb. 24, 2011

(30) Foreign Application Priority Data

Apr. 30, 2008 (JP) ................................. 2008-118969

(51) Int. Cl.
*G06K 9/00* (2006.01)
(52) U.S. Cl. ...................................................... 382/132
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS 6,243,439 B1 * 6/2001 Arai et al. ........................ 378/20
(Continued)

FOREIGN PATENT DOCUMENTS

| EP | 1 372 116 A | 12/2003 |
|---|---|---|
| JP | S54-113292 | 9/1979 |

(Continued)

OTHER PUBLICATIONS

"VoxeLine: a software program for 3D . . . " by Barrou Diallo et al. in Computerized Medical Imaging and Graphics 22 published by Elsevier Science Ltd. in 1998, p. 275-289.

(Continued)

*Primary Examiner* — Atiba O Fitzpatrick
(74) *Attorney, Agent, or Firm* — DLA Piper LLP (US)

(57) ABSTRACT

A medical X-ray CT imaging apparatus is capable of performing efficient CT imaging of living organs symmetrically located with respect to a predetermined plane. The medical X-ray CT imaging apparatus comprises an X-ray source (10), an X-ray detection means (20), a supporting means (30), a subject holding means (40), a rotation means (60*r*), a moving means (60), an imaging region specifying means for specifying imaging regions of a first living organ and a second living organ which are symmetrically located with respect to a predetermined plane, a calculation means which uses the moving means (60) and the rotation means (60*r*) to automatically and consecutively perform X-ray CT imaging of respective imaging regions of the first living organ and the second living organ, which are specified by the imaging region specifying means, and reconstructs respective CT images of the first living organ and the second living organ on the basis of electrical signals obtained by the X-ray CT imaging, and a display part (88) for displaying the CT images of the first living organ and the second living organ, which are obtained by the calculation means.

15 Claims, 29 Drawing Sheets

U.S. PATENT DOCUMENTS

| | | |
|---|---|---|
| 2004/0066877 A1 | 4/2004 | Arai et al. |
| 2005/0117696 A1 | 6/2005 | Suzuki et al. |
| 2007/0161886 A1 | 7/2007 | Kuth et al. |

FOREIGN PATENT DOCUMENTS

| | | |
|---|---|---|
| JP | H07-23946 | 1/1995 |
| JP | H7-23946 A | 1/1995 |
| JP | 2005-80748 | 3/2005 |
| JP | 2005-80748 A | 3/2005 |
| JP | 2006-149446 | 6/2006 |
| JP | 3807833 | 8/2006 |
| JP | 3926120 | 6/2007 |
| JP | 2007-325853 | 12/2007 |
| JP | 2007-325853 A | 12/2007 |
| JP | 2008-237895 A | 10/2008 |
| WO | WO 2007/102510 A | 9/2007 |

OTHER PUBLICATIONS

"Visualization in biomedical computing" by Richard A. Robb in Parallel Computing published by Elsevier Science B.V. in 1999, pp. 2067-2110.

* cited by examiner

F I G. 1
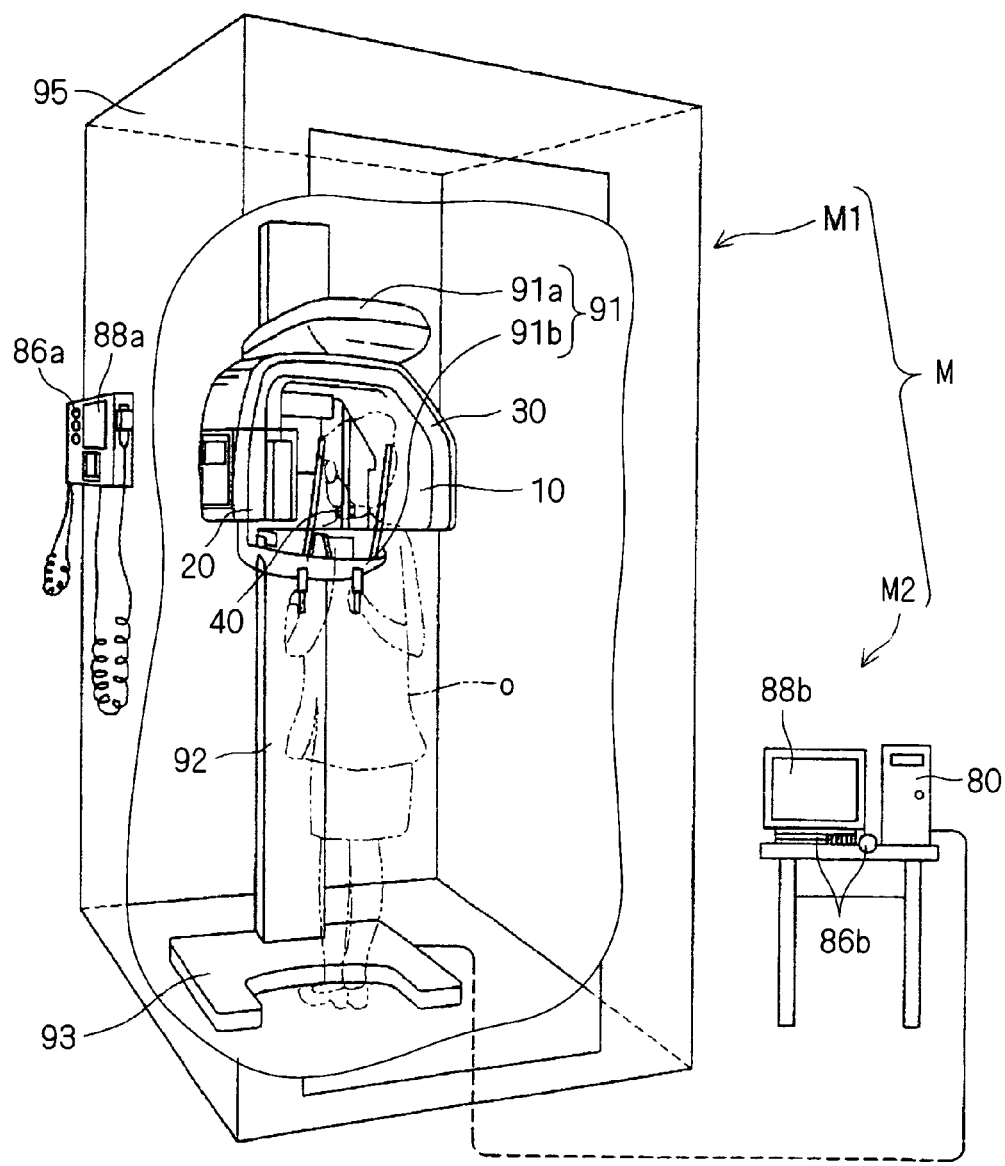

F I G. 5
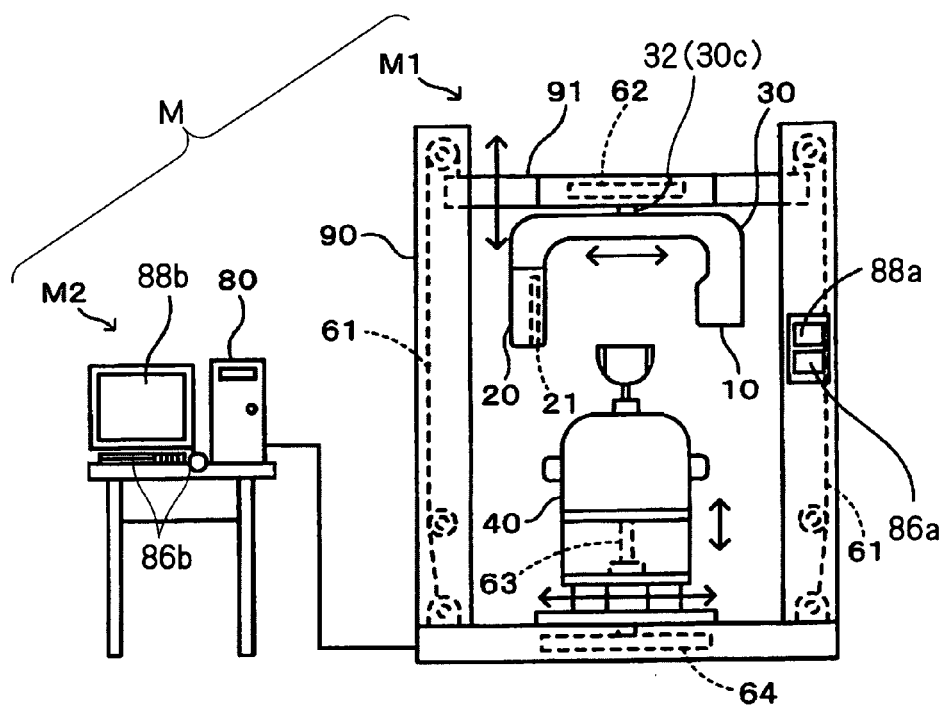
F I G. 6
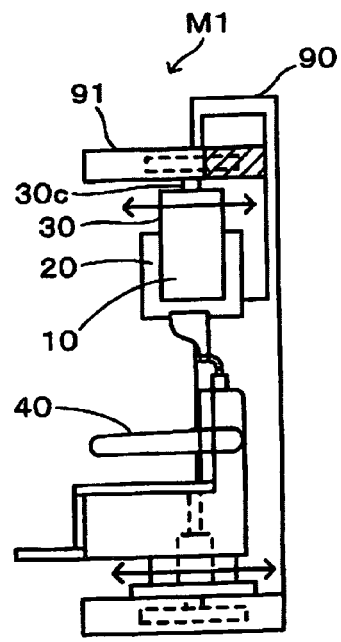

F I G . 1 3
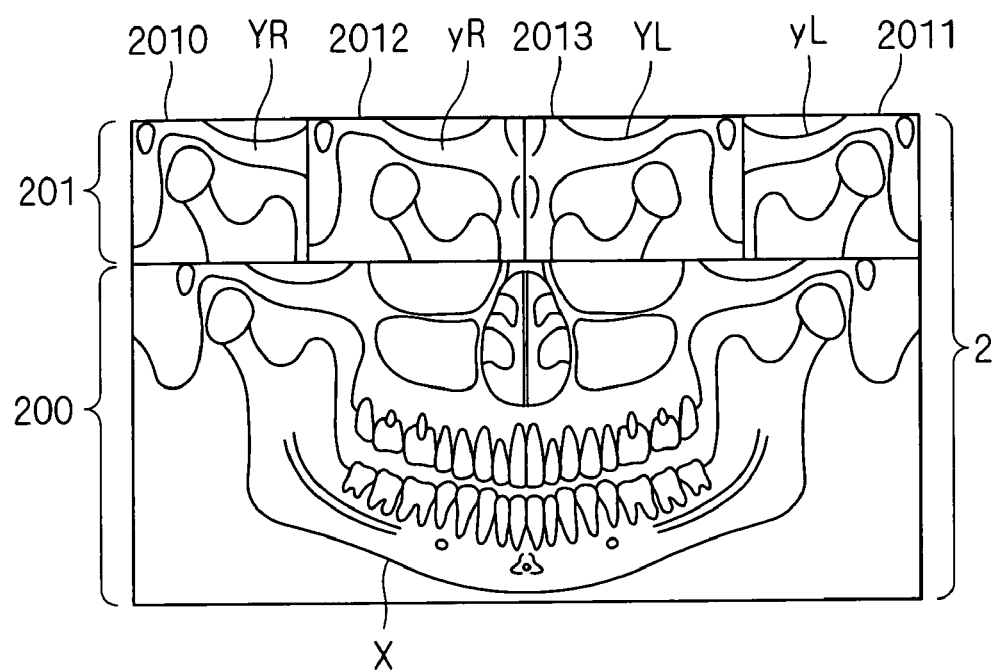

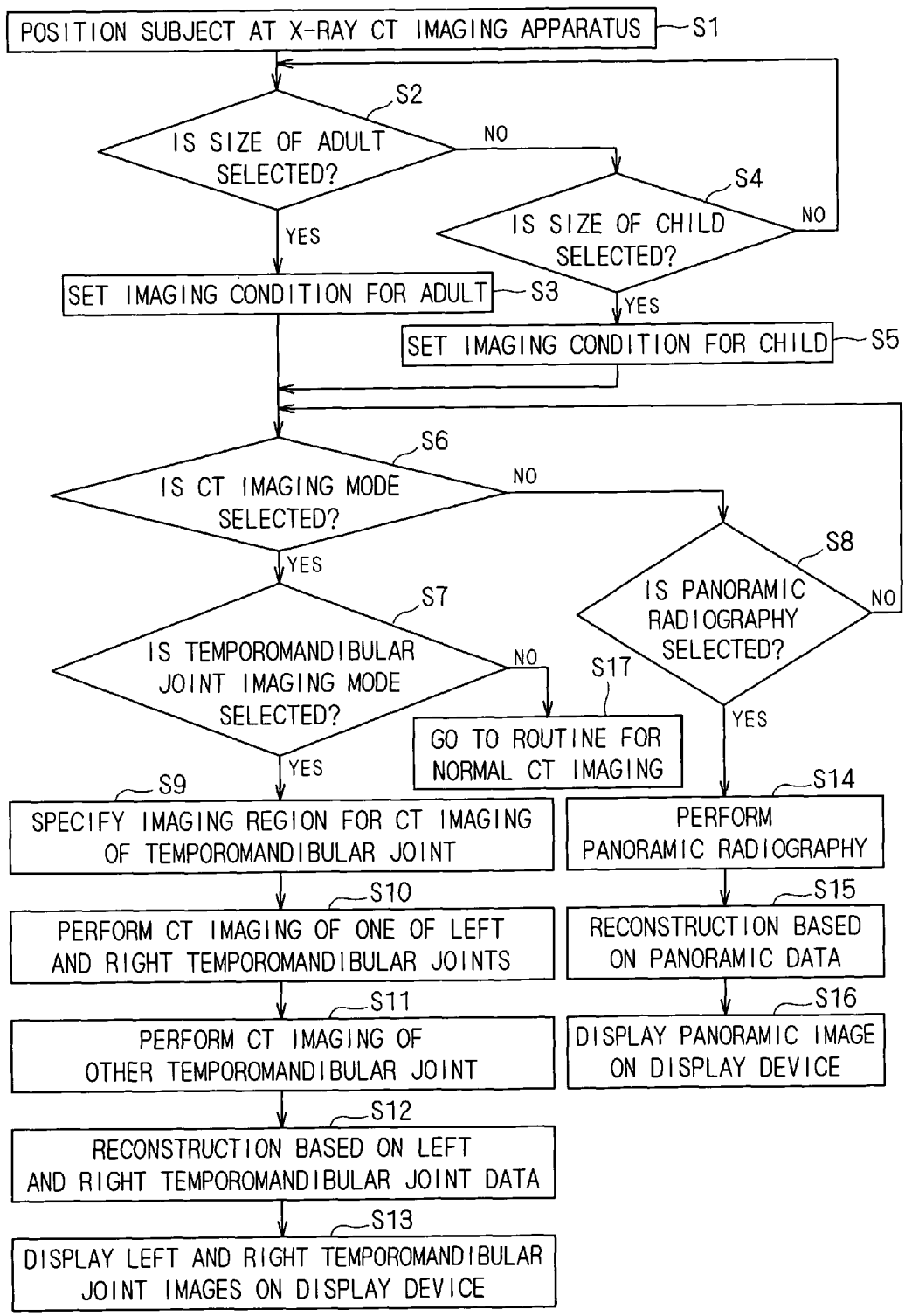

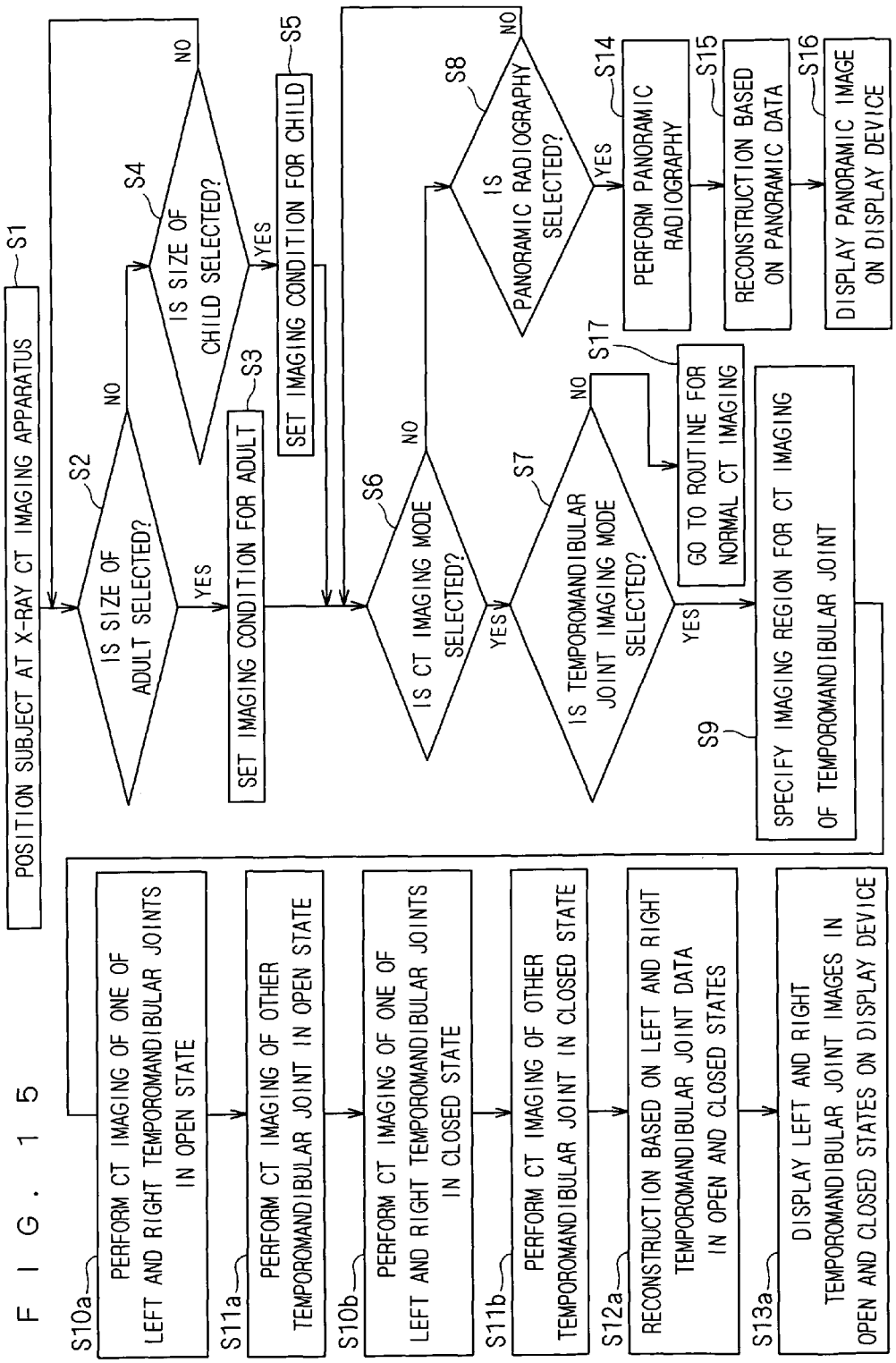

F I G . 3 2
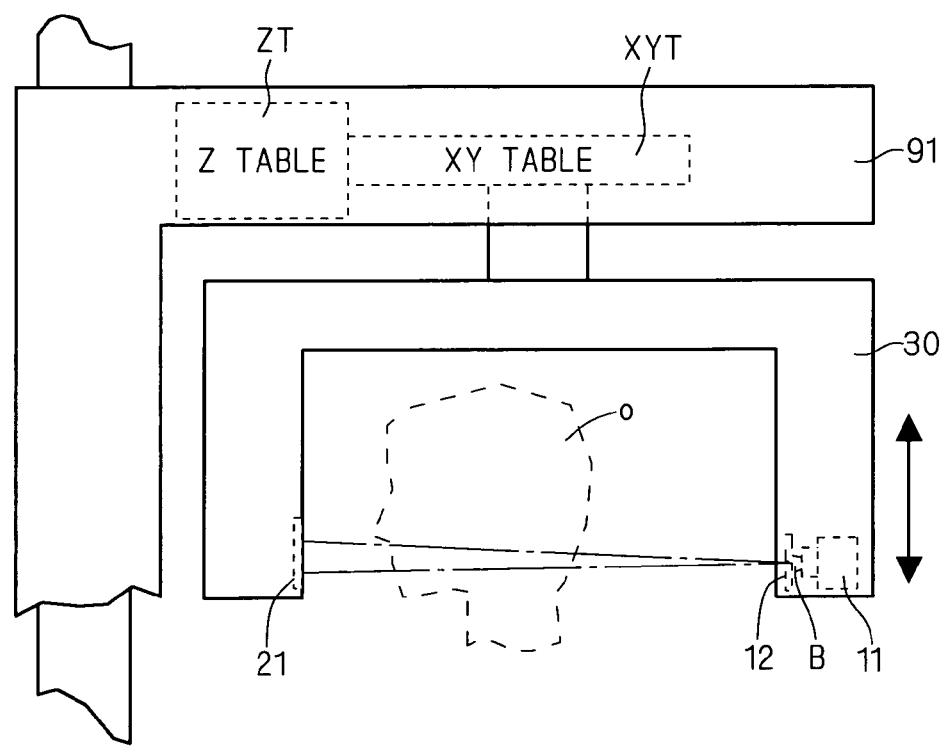

MEDICAL X-RAY CT IMAGING APPARATUS

TECHNICAL FIELD

The present invention relates to a medical X-ray CT imaging apparatus, and more particularly to a medical X-ray CT imaging apparatus for performing CT imaging of living organs located symmetrically with respect to a predetermined plane.

BACKGROUND ART

In recent years, the development of medical X-ray CT imaging apparatuses has advanced and many apparatuses having provisions for imaging in dentistry or imaging of head including otolaryngological regions and the like have been developed and manufactured. In the field of dental X-ray CT imaging apparatus, apparatuses for combined use of not only CT imaging but also panoramic radiography (disclosed in e.g., Japanese Patent No. 3807833) have been developed. Japanese Patent Application Laid-Open Gazette No. 54-113292 discloses an example of old-type medical X-ray CT imaging apparatus which performs film radiography. The medical X-ray imaging apparatus disclosed in Japanese Patent Application Laid-Open Gazette No. 54-113292 is a dental panoramic radiography apparatus having a function of temporomandibular joint radiography, which is capable of both radiography of temporomandibular joints in open and closed states and panoramic radiography thereof. The X-ray imaging apparatus disclosed in Japanese Patent Application Laid-Open Gazette No. 54-113292, however, is not an X-ray CT imaging apparatus and therefore the apparatus cannot reconstruct the cross sections of the temporomandibular joints from an arbitrary direction.

As another example of medical X-ray CT imaging apparatus, Japanese Patent Application Laid-Open Gazette No. 2006-149446 discloses an X-ray CT imaging apparatus, which is used for diagnosis of organs located at left and right sides of a spine as a center. The X-ray CT imaging apparatus disclosed in Japanese Patent Application Laid-Open Gazette No. 2006-149446 has a technology for extracting portions which are symmetrically located at left and right sides of a spinal cord as a center line. Japanese Patent No. 3926120 discloses an apparatus for specifying a region of interest on a schematic view of a subject as an imaging target region and performing X-ray CT imaging of the imaging target region.

DISCLOSURE OF INVENTION

In order to perform X-ray CT imaging of living organs (for example, temporomandibular joints or otolaryngological regions) which are symmetrically located with respect to a predetermined plane (for example, a section plane including a median line by which a living body is divided into left and right sides or an occlusal surface of a head), conventional medical X-ray CT imaging apparatuses need to separately capture the images of the living organs or perform an additional operation of extracting symmetrically-located portions out of the captured CT images. Further, in order to compare the CT images of the living organs which are symmetrically located with respect to a predetermined plane with each other, the conventional medical X-ray CT imaging apparatuses require operator's operation for displaying the CT images for comparison and therefore cannot support efficient diagnoses or effective explanations for patients.

It is an object of the present invention to provide a medical X-ray CT imaging apparatus capable of X-ray CT imaging of living organs which are symmetrically located with respect to a predetermined plane.

In order to solve the above problems, a medical X-ray CT imaging apparatus according to a first aspect of the present invention comprises an X-ray source for generating a cone beam, an X-ray detection part for detecting the cone beam, a supporting part for arranging the X-ray source and the X-ray detection part to be opposed to each other with a subject interposed therebetween, a subject holding part for holding the subject, a rotation driving part for driving the supporting part and the subject holding part to rotate relative to each other, an axis moving part for causing the rotation axis of the rotation driving part to be movable relative to the subject, a control part for automatically and consecutively performing X-ray CT imaging of respective imaging regions specified for a first living organ and a second living organ which are symmetrically located with respect to a predetermined plane by using the axis moving part and the rotation driving part, an image processing part for reconstructing respective CT images of the first living organ and the second living organ on the basis of an electrical signal obtained by the X-ray detection part through the X-ray CT imaging, and a display part for displaying the CT images of the first living organ and the second living organ which are obtained by the image processing part.

Since the CT imaging can be automatically performed consecutively on the imaging regions specified for both the first living organ and the second living organ, the operational load of an operator can be reduced. The medical X-ray CT imaging apparatus according to the present invention can be configured to perform local CT imaging on only part of the subject as the imaging region, and it is therefore possible to reduce the radiation exposure dose for the respective imaging regions of the first living organ and the second living organ and perform X-ray CT imaging with high resolution. Further, the medical X-ray CT imaging apparatus according to claim 1 of the present invention may have such a size as to occupy the same area as that of the conventional dental panoramic radiography apparatus and as to be housed in an X-ray proof chamber of a dental clinic or the like.

According to a second aspect of the present invention, the medical X-ray CT imaging apparatus of the first aspect further comprises an imaging region specifying part for specifying respective imaging regions for the first living organ and the second living organ.

Since the imaging regions can be specified for both the first living organ and the second living organ, it is possible to specify desired imaging regions.

According to a third aspect of the present invention, in the medical X-ray CT imaging apparatus of the first or second aspect, X-ray CT imaging of a third living organ located between the first living organ and the second living organ is performed, and the X-ray CT imaging of the third living organ is automatically performed consecutively before or after the X-ray CT imaging of the first living organ and the second living organ or between the X-ray CT imaging of the first living organ and the X-ray CT imaging of the second living organ.

Since the X-ray CT imaging can be automatically and consecutively performed not only on the first living organ and the second living organ but also on another portion, i.e., the third living organ, the operational load of the operator can be further reduced when it is intended to perform the CT imaging on another portion as well as the first living organ and the second living organ.

According to a fourth aspect of the present invention, in the medical X-ray CT imaging apparatus of any one of the first to third aspects, the rotation driving part and the axis moving part perform panoramic radiography in conjunction with the movement of the rotation axis.

The apparatus, which is capable of performing panoramic radiography, can be used for several functions, and this ensures high use efficiency of the apparatus.

According to a fifth aspect of the present invention, the medical X-ray CT imaging apparatus of any one of the first to fourth aspects further comprises a storage part for storing the CT image of the first living organ and the CT image of the second living organ which are captured consecutively by the X-ray CT imaging while associating the CT images with each other.

Since the storage part stores the CT image of the first living organ and the CT image of the second living organ while associating the CT images with each other, it is possible to manage the CT images of the first and second living organs as a pair of data, and therefore the apparatus has the effect of simplifying data management.

According to a sixth aspect of the present invention, in the medical X-ray CT imaging apparatus of the second aspect, the imaging region specifying part displays an illustration including at least the first living organ and the second living organ on the display part, to specify the imaging regions on the basis of the illustration.

Since the operator can specify the imaging region on the basis of the illustration of the living organ, the apparatus has the effect of ensuring easy specification of imaging regions.

According to a seventh aspect of the present invention, the medical X-ray CT imaging apparatus of any one of the first to sixth aspects further comprises an imaging condition changing part for selecting whether the subject is an adult or a child and changing the condition for the X-ray CT imaging according to the selection.

Since the imaging condition changing part selects whether the subject is an adult or a child and changes the imaging condition, the apparatus has the effect of achieving automatic control on the tube current, the tube voltage, and the like of an optimal X-ray power supply. In the medical X-ray CT imaging apparatus according to claim 5 of the present invention, by selecting adult or child, it is possible to automatically determine roughly the positions of the first and second living organs, i.e., the respective center positions of the imaging regions (on the basis of the factory setting value).

According to an eighth aspect of the present invention, in the medical X-ray CT imaging apparatus of any one of the first to seventh aspects, the first living organ and the second living organ are temporomandibular joints or otolaryngological regions.

Since the temporomandibular joints or the living organs of the otolaryngological regions are living organs symmetrically located with respect to a predetermined plane in many cases, the apparatus has the effect of supporting efficient diagnoses.

According to a ninth aspect of the present invention, in the medical X-ray CT imaging apparatus of the eighth aspect, the first living organ and the second living organ are the temporomandibular joints, and the X-ray CT imaging of the temporomandibular joints is performed consecutively on either one of open and closed states thereof and then on the other state.

Since imaging can be performed consecutively on the open state and the closed state, the smoothness of the temporomandibular joints can be checked, and therefore the apparatus has the effect of supporting more accurate diagnoses.

According to a tenth aspect of the present invention, in the medical X-ray CT imaging apparatus of the ninth aspect, the display part displays the CT images of the first living organ and the second living organ in the open state and the CT images of these living organs in the closed state on one display screen for comparison.

Since the CT images on the open state and the closed state can be displayed on one screen for comparison, it is possible to make a diagnosis while observing the change between in the open state and in the closed state, and therefore the apparatus has the effect of supporting efficient diagnoses and effective explanations for patients.

According to an eleventh aspect of the present invention, in the medical X-ray CT imaging apparatus of the ninth aspect, the CT images of the temporomandibular joints captured by the X-ray CT imaging, from the open state to the closed state, are displayed on the display part as a moving image.

Since the CT images from the open state to the closed state can be displayed as a moving image, it is possible to make a diagnosis while observing an actual movement of the living organ, and therefore the apparatus has the effect of supporting efficient diagnoses and effective explanations for patients.

According to a twelfth aspect of the present invention, in the medical X-ray CT imaging apparatus of any one of the first to eleventh aspects, the display part displays the CT images of the first living organ and the second living organ on one display screen for comparison.

Since the display part displays the CT images of the first living organ and the second living organ on one screen for comparison, it is possible to take a view of the CT images, and therefore the apparatus has the effect of supporting efficient diagnoses and effective explanations for patients.

According to a thirteenth aspect of the present invention, in the medical X-ray CT imaging apparatus of second or sixth aspects, at least one of the X-ray source and the axis moving part is adjusted on the basis of the sizes of the first living organ and the second living organ specified by the imaging region specifying part.

Since at least one of the X-ray source and the axis moving part can be adjusted on the basis of the sizes of the first and second living organs specified by the imaging region specifying part, it is possible to reduce the radiation exposure dose for the imaging regions.

According to a fourteenth aspect of the present invention, in the medical X-ray CT imaging apparatus of any one of the first to thirteenth aspects, the display part displays a CT image obtained by combining CT imaging data of the first living organ and the second living organ and arranging the CT imaging data in accordance with the actual three-dimensional positions of the first living organ and the second living organ.

Since the first living organ and the second living organ are displayed in accordance with the actual arrangement, good visibility can be achieved for recognition of the positions of these two living organs.

According to a fifteenth aspect of the present invention, in the medical X-ray CT imaging apparatus of the third aspect, the display part displays a CT image obtained by combining CT imaging data of the first living organ, the second living organ, and the third living organ and arranging the CT imaging data in accordance with the actual three-dimensional positions of the first living organ, the second living organ, and the third living organ.

Since the first living organ, the second living organ, and the third living organ are displayed in accordance with the actual arrangement, good visibility can be achieved for recognition of the positions of these three living organs.

BRIEF DESCRIPTION OF DRAWINGS

FIG. 1 is a schematic view showing a medical X-ray CT imaging apparatus M in accordance with a first preferred embodiment of the present invention;

FIGS. 5 and 6 are schematic views showing the medical X-ray CT imaging apparatus M in accordance with the first preferred embodiment of the present invention;

FIG. 13 is a view showing a display screen of the medical X-ray CT imaging apparatus M in accordance with the first preferred embodiment of the present invention;

FIGS. 14 and 15 are flowcharts showing an operation of the medical X-ray CT imaging apparatus M in accordance with a second preferred embodiment of the present invention;

FIGS. 28 to 32 are views showing a state of emission of cone beams;

BEST MODE FOR CARRYING OUT THE INVENTION

The First Preferred Embodiment

Figure 2:
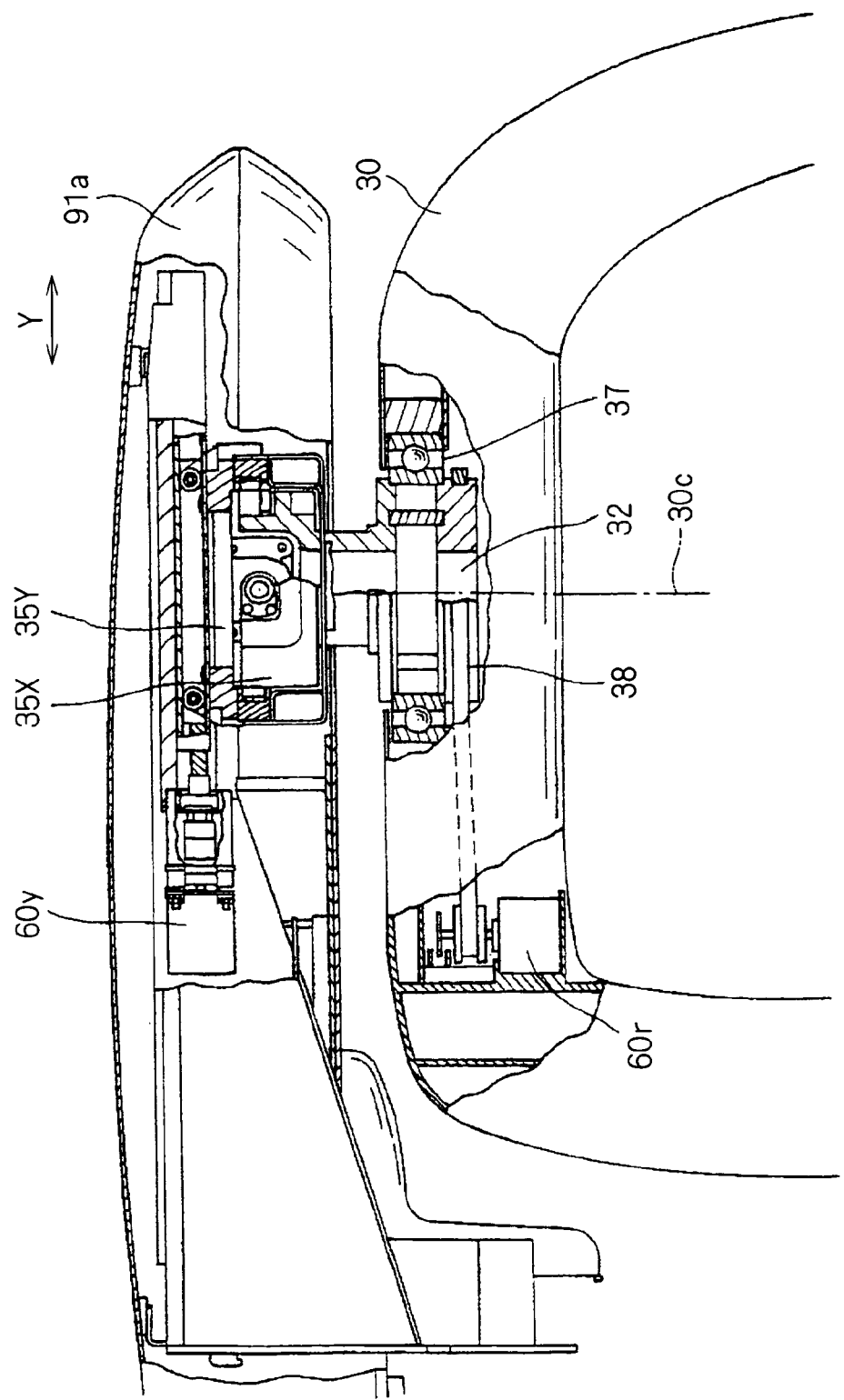
FIGS. 2 to 4 are schematic views showing a supporting part and a driving part of the medical X-ray CT imaging apparatus M in accordance with the first preferred embodiment of the present invention.

A medical X-ray CT imaging apparatus in accordance with the first preferred embodiment is capable of automatically and consecutively performing CT imaging of living organs (for example, temporomandibular joints or otolaryngological regions) which are symmetrically located with respect to a predetermined plane (for example, a section plane including a median line by which a living body is divided into left and right sides or an occlusal surface of a head) and displaying CT images of the living organs which are captured by CT imaging for comparison. The CT images include a tomography image and a volume rendering image of each of the living organs symmetrically located with respect to the predetermined plane.

FIG. 1 is a view showing a medical X-ray CT imaging apparatus in accordance with the first preferred embodiment. The medical X-ray CT imaging apparatus M of FIG. 1 includes an X-ray imaging apparatus body M1 and an X-ray image display device M2. The X-ray imaging apparatus body M1 comprises a supporting part 30 which is a rotation arm incorporating a rotation motor, supporting an X-ray generation part 10 and an X-ray detection part 20 which are provided at the ends of the supporting part 30 and opposed to each other. In order to move the supporting part 30 up and down, the supporting part 30 is suspended from an up-and-down moving frame 91. The up-and-down moving frame 91 is provided with respect to a column 92 standing right from a base 93 and has an upper frame 91a from which the supporting part 30 is suspended and a lower frame 91b for holding a subject o, which are configured to form a substantially squared U-shape projecting forward. The up-and-down moving frame 91 is movable up and down by means of a not-shown up-and-down moving mechanism and incorporates an XY table (not shown) for horizontally moving the rotation axis of the supporting part 30.

The lower frame 91b comprises a subject holding part 40 including an ear rod for fixing a human head which is a subject o from the left and right sides, a chin rest for fixing a chin, and the like. The subject o is introduced in the subject holding part 40 at an appropriate position by moving the supporting part up or down in accordance with the height of the subject o. The X-ray imaging apparatus body M1 of FIG. 1 is housed in an X-ray proof chamber 95, and at the outer wall of the X-ray proof chamber 95, attached is an operation panel 86a provided with a small-sized liquid crystal panel serving as a display part 88a. The X-ray image display device M2 of FIG. 1 is configured to transfer data between itself and the X-ray imaging apparatus body M1 via a communication cable. The X-ray image display device M2 includes of e.g., a computer and a workstation, and a display device body 80 is provided with a display part 88b formed of a display device such as a liquid crystal monitor and an operation part 86b including a keyboard, a mouse, and the like. Various commands can be given through a mouse pointer operation or the like on characters or images displayed on the display part 88b. The display part 88b may be formed of a touch panel, and therefore the display part 88b also serves as the operation part 86b in this case.

FIG. 2 is a partially sectional view showing the supporting part 30 and the upper frame 91a. The upper frame 91a comprises a table (Y table) 35Y which moves in a fore-and-aft direction (Y direction), a table (X table) 35X which is supported by the Y table 35Y and moves in a horizontal direction (X direction), a Y-axis motor 60y of the Y direction for moving the Y table 35Y in the Y direction, an X-axis motor (not shown) for moving the X table 35X in the X direction relative to the Y table 35Y, and a rotation motor 60r for rotating the supporting part 30 about a rotation axis 30c which is the axis center of an axis 32 coupling the X table 35X and the supporting part 30. A bearing 37 is provided between the axis 32 and the supporting part 30, thereby facilitating the rotation of the supporting part 30 about the axis 32. The rotation motor 60r is fixed inside the supporting part 30 and transmits the rotation force via a belt 38 to the axis 32, to thereby rotate the supporting part 30. The mechanism including the axis 32, the bearing 37, the belt 38, and the rotation motor 60r is an exemplary rotation mechanism for rotating the supporting part 30. By driving three control motors in accordance with a predetermined program, it is possible to move the XY table (35X, 35Y) in the fore-and-aft (Y) direction and the left and right (X) direction while rotating the supporting part 30.

Figure 3:
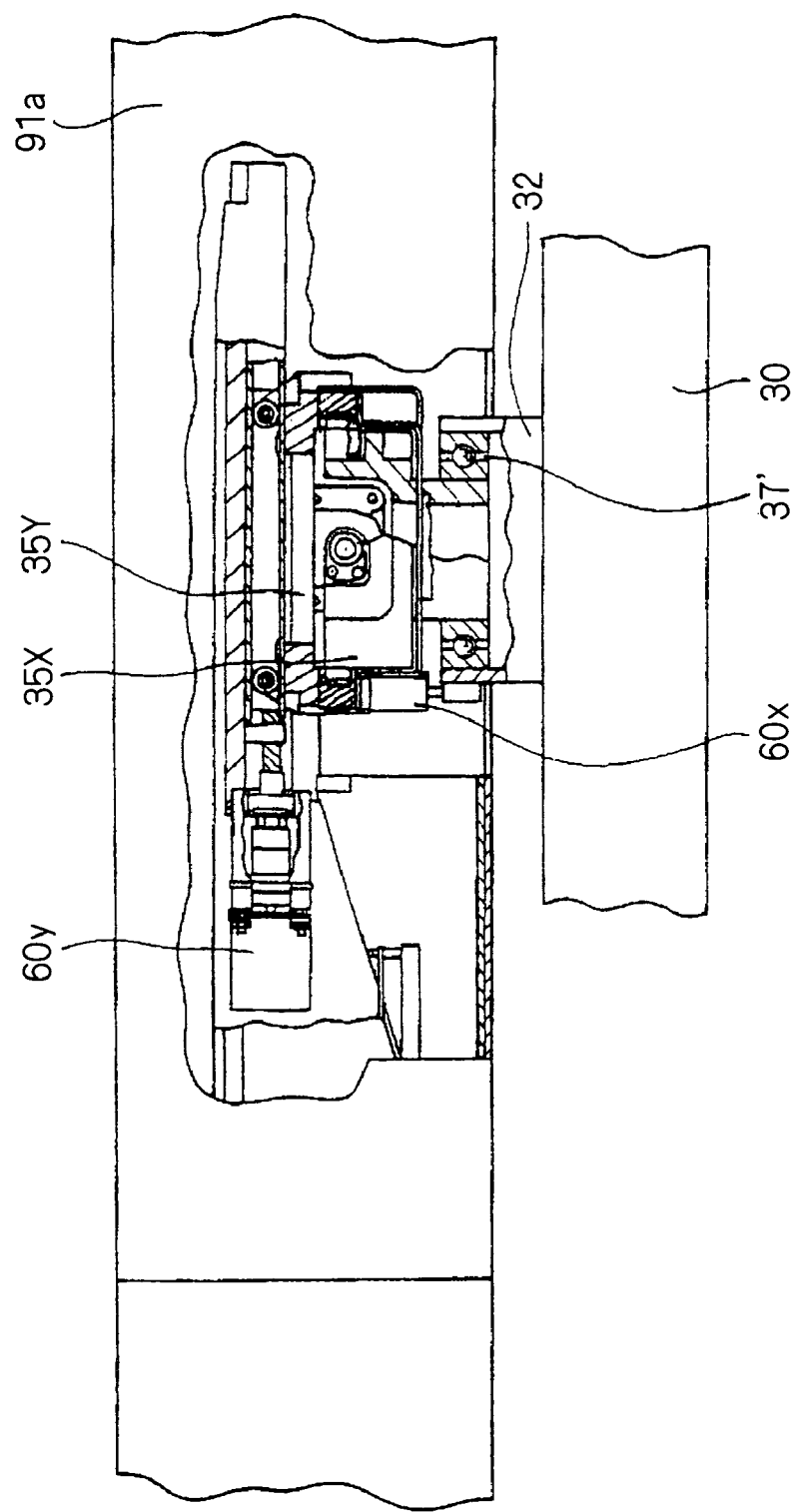

The mechanism of FIG. 2 for rotating and moving the supporting part 30 is an exemplary one. The present invention is not limited to this exemplary mechanism but such a mechanism including another supporting part 30 and another upper frame 91a as shown in FIG. 3 may be used. The mechanism of FIG. 3 is mostly the same as that shown in FIG. 2 but different therefrom in construction of a rotation mechanism for rotating the supporting part 30. The upper frame 91a comprises the table (Y table) 35Y which moves in the fore-and-aft direction (Y direction), the table (X table) 35X which is supported by the Y table 35Y and moves in the horizontal direction (X direction), the Y-axis motor 60y of the Y direction for moving the Y table 35Y in the Y direction, the X-axis motor 60x (not shown in FIG. 2) for moving the X table 35X in the X direction relative to the Y table 35Y, and the rotation motor 60r for rotating the supporting part 30 about the rotation axis 30c which is the axis center of the axis 32 coupling the X table 35X and the supporting part 30. The upper frame 91a of FIG. 3 further comprises the axis 32 coupling the X table 35X and the supporting part 30 and a bearing 37' provided between the axis 32 and the supporting part 30. The rotation axis of the rotation motor 60r comes into contact with the outer perimeter of the axis 32 fixed on the supporting part 30 to transmit the rotation force to the axis 32, whereby the supporting part 30 rotates about the rotation axis 30c.

Figure 4:
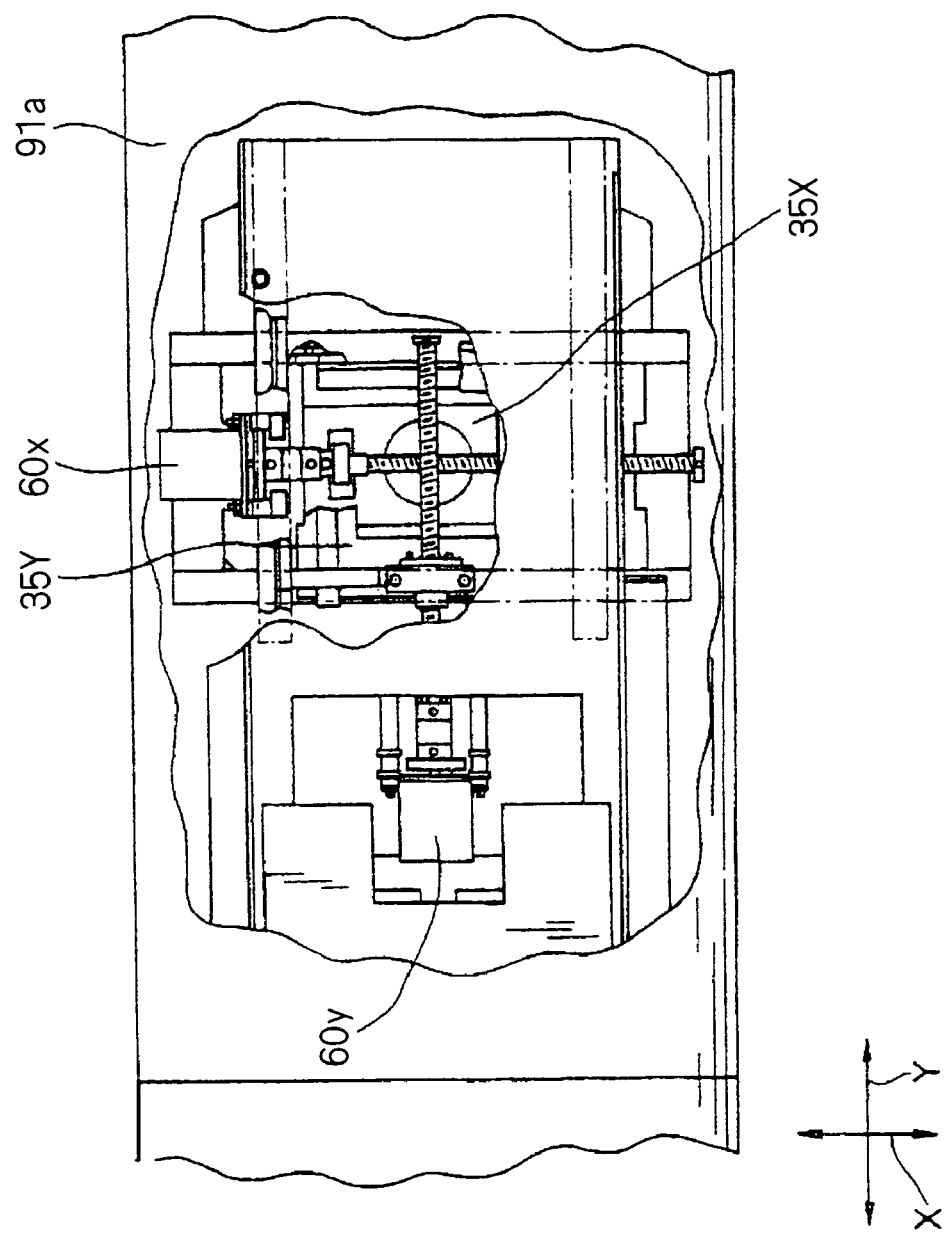

FIG. 4 is a plain view of the XY table (35X, 35Y) shown in FIGS. 2 and 3. FIG. 4 shows the arrangement of the table (Y table) 35Y which moves in the fore-and-aft direction (Y direction), the table (X table) 35X which is supported by the Y table 35Y and moves in the horizontal direction (X direction), the Y-axis motor 60y of the Y direction for moving the Y table in the Y direction, the X-axis motor 60x for moving the X table in the X direction relative to the Y table. In the above-discussed case, for convenience of coordinate calculation for control, the X direction and the Y direction are orthogonal to each other, but the two directions may be crossed at an arbitrary angle, instead of right angle, only if the two-dimensional control can be made.

The medical X-ray CT imaging apparatus of the present invention is not limited to the medical X-ray CT imaging apparatus M shown in FIG. 1 but may be another medical X-ray CT imaging apparatus M shown in FIGS. 5 and 6. FIG. 5 is an elevational view of another medical X-ray CT imaging apparatus M and FIG. 6 is a side elevation of the medical X-ray CT imaging apparatus M of FIG. 5. The X-ray imaging apparatus body M1 shown in FIGS. 5 and 6 comprises the supporting part 30 which is rotated by the rotation motor 60r (not shown) and supports the X-ray generation part 10 and the X-ray detection part 20 which are provided at the ends of the supporting part 30 and opposed to each other and the subject holding part 40 which is formed like a seat and comprises a headrest or a holder for fixing a human head which is the subject o, and the supporting part 30 and the subject holding part 40 are displaceably attached to a fixed frame 90 formed like an arch.

More specifically, the supporting part 30 is attached to the fixed frame 90 with the up-and-down moving frame 91 interposed therebetween. The up-and-down moving frame 91 which is vertically movable by means of a chain drive part 61 incorporates an XY table 62 for two-dimensionally moving the axis 32 (rotation axis 30c) about which the supporting part 30 is rotated, specifically in this case, for moving the axis 32 horizontally in the X direction and the Y direction. The subject holding part 40 is supported at the bottom thereof from below by a up-and-down moving part 63 which is movable up and down, and the bottom of the fixed frame 90 incorporates an XY table 64 for horizontally moving the up-and-down moving part 63, like the XY table 62. At the column of the fixed frame 90, attached are the display part 88a formed of a liquid crystal monitor, a small-sized liquid crystal panel, or the like and the operation panel 86a including a plurality of operation buttons and the like. An X-ray detector 21 is a device for detecting an X-ray, which is attached to the X-ray detection part 20.

Next, the medical X-ray CT imaging apparatus M of the first preferred embodiment will be described with reference to the block diagram of FIG. 7. The medical X-ray CT imaging apparatus M comprises the X-ray imaging apparatus body M1 and the X-ray image display device M2 and transfers data therebetween via the communication cable.

Only if data can be transferred, wireless communication may be adopted.

The X-ray imaging apparatus body M1 comprises the supporting part 30 supporting the X-ray generation part 10 and the X-ray detection part 20 which are opposed to each other, a driving part 60 for driving the supporting part 30, and an imaging apparatus body control part 70. The imaging apparatus body control part 70 is provided with the display part 88a and the operation part 86a. The operation part 86a may be also used to specify the positions or the like of living organs (imaging regions) which are symmetrically located with respect to a predetermined plane.

The X-ray generation part 10 includes an X-ray source, i.e., an X-ray generator 11, formed of an X-ray tube for emitting an X-ray and the like and a radiation field control part 12 formed of a slit, a collimator, and the like for limiting the spread of X-ray beams B. The X-ray detection part 20 is formed of a cassette 22 provided with an X-ray detector 21 serving to detect the X-ray emitted from the X-ray generator 11 and including MOS sensors, CCD sensors, or the like which two-dimensionally spread out. The cassette 22 is detachable/attachable from/to the X-ray detection part 20, and the X-ray detector 21 may be fixed to the X-ray detection part 20 without the cassette 22 interposed therebetween. The driving part 60 comprises the X-axis motor 60x and the Y-axis motor 60y which work together to horizontally move the rotation axis 30c of the supporting part 30 and the rotation motor 60r for rotating the supporting part 30. The rotation motor 60r may rotate the axis 32 fixed to the supporting part 30 or the rotation motor 60r may rotate the supporting part 30 in a structure wherein the supporting part 30 is rotatable about the axis 32 only if driving is made so that the supporting part can be rotated about the rotation axis 30c.

Similarly, the X-axis motor 60x and the Y-axis motor 60y may move the axis 32 horizontally with respect to the above-described up-and-down moving frame 91, or the X-axis motor 60x and the Y-axis motor 60y may move the supporting part 30 horizontally with respect to the axis 32 in a structure wherein the supporting part 30 is movable horizontally with respect to the axis 32. The rotation motor 60r, the X-axis motor 60x, and the Y-axis motor 60y constitute the driving part 60 serving as a driving source for moving the supporting part 30 relatively with respect to the subject o. The imaging apparatus body control part 70 is formed of a CPU 71 for executing various control programs including a control program used for controlling the driving part 60 and comprises an X-ray generation part control part 72 for controlling the X-ray generation part 10 and an X-ray detection part control part 73 for controlling the X-ray detection part 20. The control part 70 of the X-ray imaging apparatus body M1 and a CPU 81 which is a constituent element of a control part of the X-ray image display device M2 collectively constitute a control part 70a. The operation panel 86a including a plurality of operation buttons and the like. As an input part used as a substitute for the operation panel 86a or used together with the operation panel 86a, an input part such as a keyboard, a mouse, a touch pen, or the like may be used besides the operation buttons. There may be a configuration wherein a voice command is received through a microphone and recognized. In other words, the operation panel 86a is an example of the operation part 86, and any element can be used as the operation part 86 only if it can receive the operation of an operator. The display part 88a is a display such as a liquid crystal monitor.

For example, there may be a case where information such as characters or images required for the operation of the X-ray imaging apparatus body M1 is displayed on the display part 88a, or there may be another case where the X-ray imaging apparatus body M1 is connected to the X-ray image display device M2 and the content displayed on the display part 88b of the X-ray image display device M2 is also displayed on the display part 88a. There may still another case where various commands can be given to the X-ray imaging apparatus body M1 through a pointer operation with a mouse or the like on characters or images displayed on the display part 88a. The subject holding part 40 and the driving part 60 serve as a moving mechanism part 65 for relatively moving the X-ray generator 11 and the X-ray detector 21 with respect to the subject o.

The X-ray imaging apparatus body M1 performs local CT imaging of imaging regions r (living organs symmetrically located with respect to a predetermined plane) of the subject o in accordance with the command from the operation panel 86a or the X-ray image display device M2. The X-ray imaging apparatus body M1 receives various commands, coordinate data, or the like from the X-ray image display device M2 and sends the data of captured CT image to the X-ray image display device M2.

In the X-ray image display device M2, the display part 88b and the operation part 86b are connected to the display device body 80. The display device body 80 includes the CPU 81 for executing various programs and a hard disk and the like and comprises a storage part 82 for storing various imaging data, images, or the like, an imaging region specifying part 83 for calculating the coordinates of a region specified by the operation part 86 and specifying the region as the imaging region r, and an image operation part 84 for reconstructing CT images and performing other operations. The storage part 82, the imaging region specifying part 83, and the image operation part 84 constitute an image processing part 85.

The storage part 82 can store respective CT images of living organs symmetrically located with respect to a predetermined plane, which are obtained by local CT imaging, while associating the CT images with each other. The operation panel 86a and the operation part 86b constitute the operation part 86, and the operation part 86 specifies the imaging region r. Specifically, the operator uses the operation part 86 to specify a region to be captured by the imaging in the screen (an illustration, a panoramic image, or the like) displaying part of or the whole of a living body, to thereby specify the imaging region r. In specification of the imaging region r by using the operation part 86, there may be a case where one of the living organs symmetrically located with respect to a predetermined plane is specified and the position of the other living organ is automatically obtained by the imaging region specifying part 83 or the like, or there may be another case where the operator specifies the positions of both the living organs. There may be still another case where without the operator's specification on the positions of the living organs, the operation part 86 specifies only information, an imaging target portion, or the like on the subject o and the imaging region specifying part 83 or the like automatically specifies the imaging region r. The display part 88a and the display part 88b constitute the display part 88. The imaging region r may be specified by giving an operation of the operation part 86 onto an image displayed on the screen of the display part 88 or the portion may be specified directly by using the operation part 86 to input the name of the portion or the code thereof without displaying any image for region specification on the screen.

Figure 7:
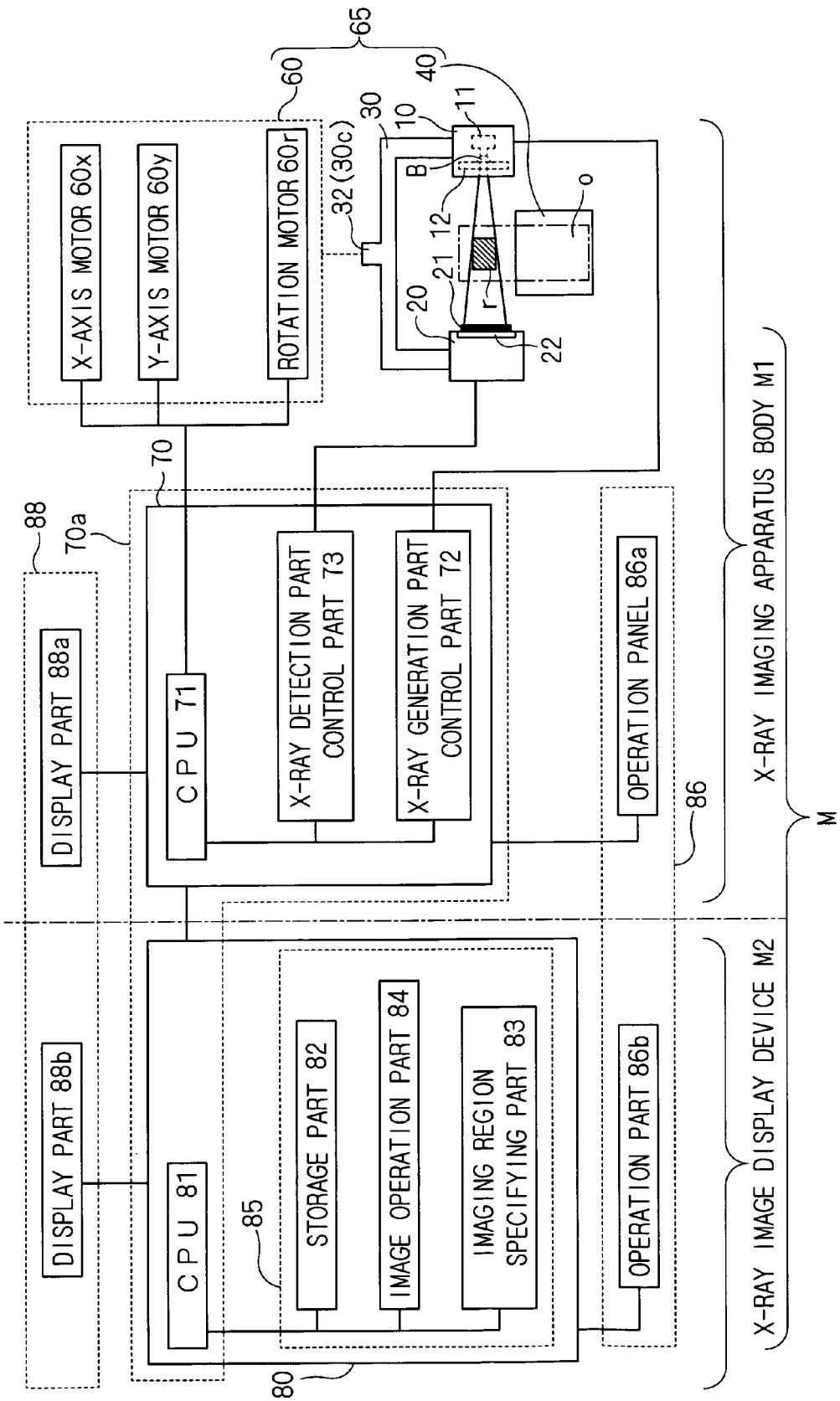
FIGS. 7 to 9 are block diagrams showing the medical X-ray CT imaging apparatus M in accordance with the first preferred embodiment of the present invention.
Figure 8:
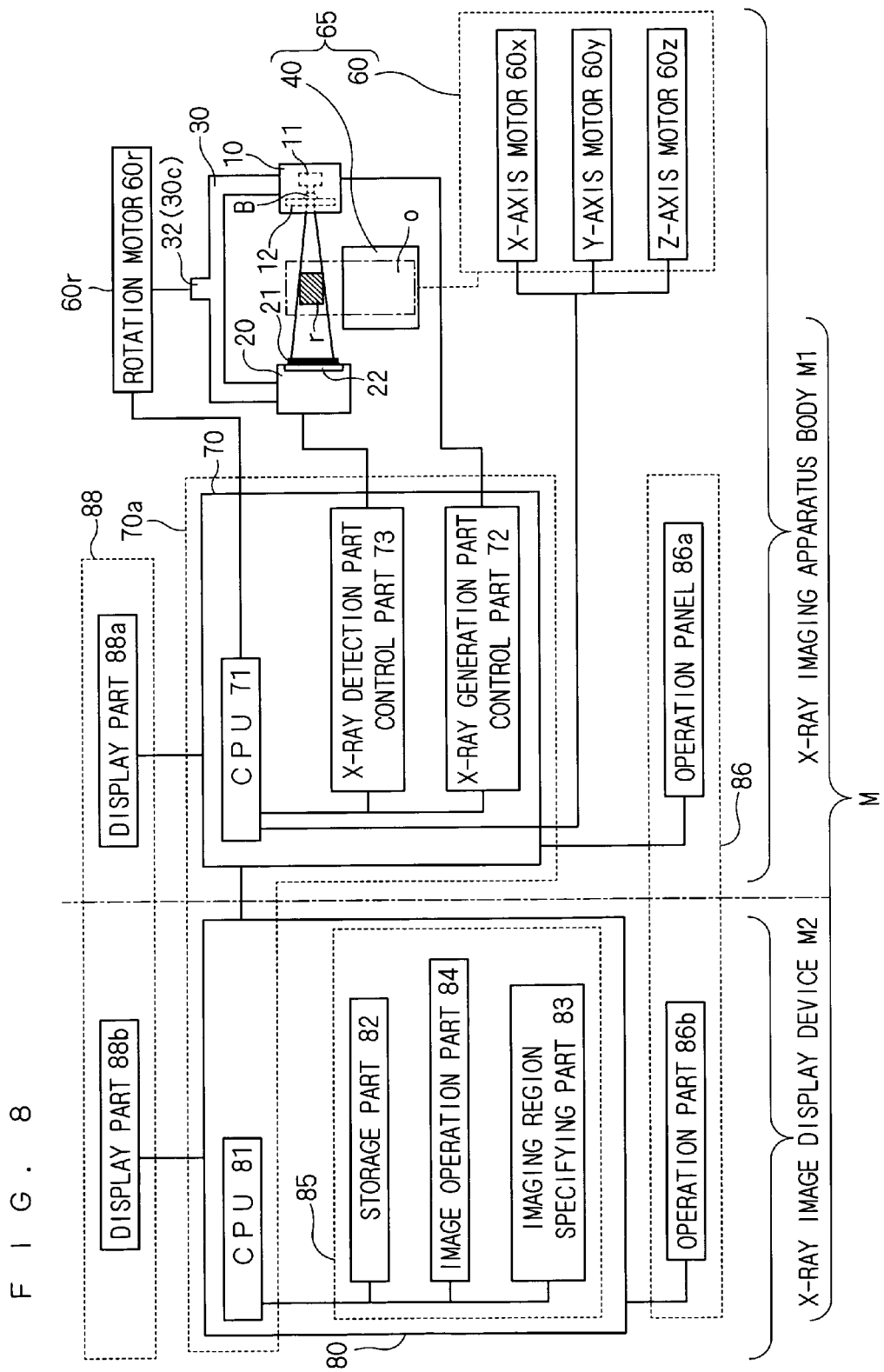

FIG. 8 is a block diagram showing a medical X-ray CT imaging apparatus M different from the medical X-ray CT imaging apparatus M shown in FIG. 7. The medical X-ray CT imaging apparatus M of FIG. 8 has the same basic configuration as that of the medical X-ray CT imaging apparatus M of FIG. 7 but is different from the medical X-ray CT imaging apparatus M of FIG. 7 in that the X-ray imaging apparatus body M1 of FIG. 8 comprises the rotation motor 60r for rotating the supporting part 30 but does not comprise the X-axis motor 60x or the Y-axis motor 60y for moving the axis 32. The medical X-ray CT imaging apparatus M of FIG. 8 is different from the medical X-ray CT imaging apparatus M of FIG. 7 further in that the X-ray imaging apparatus body M1 of FIG. 8 comprises an X-axis motor 60x and a Y-axis motor 60y both for horizontally moving the subject o held by the subject holding part 40 and a Z-axis motor 60z for moving the subject holding part 40 up and down.

Figure 9:
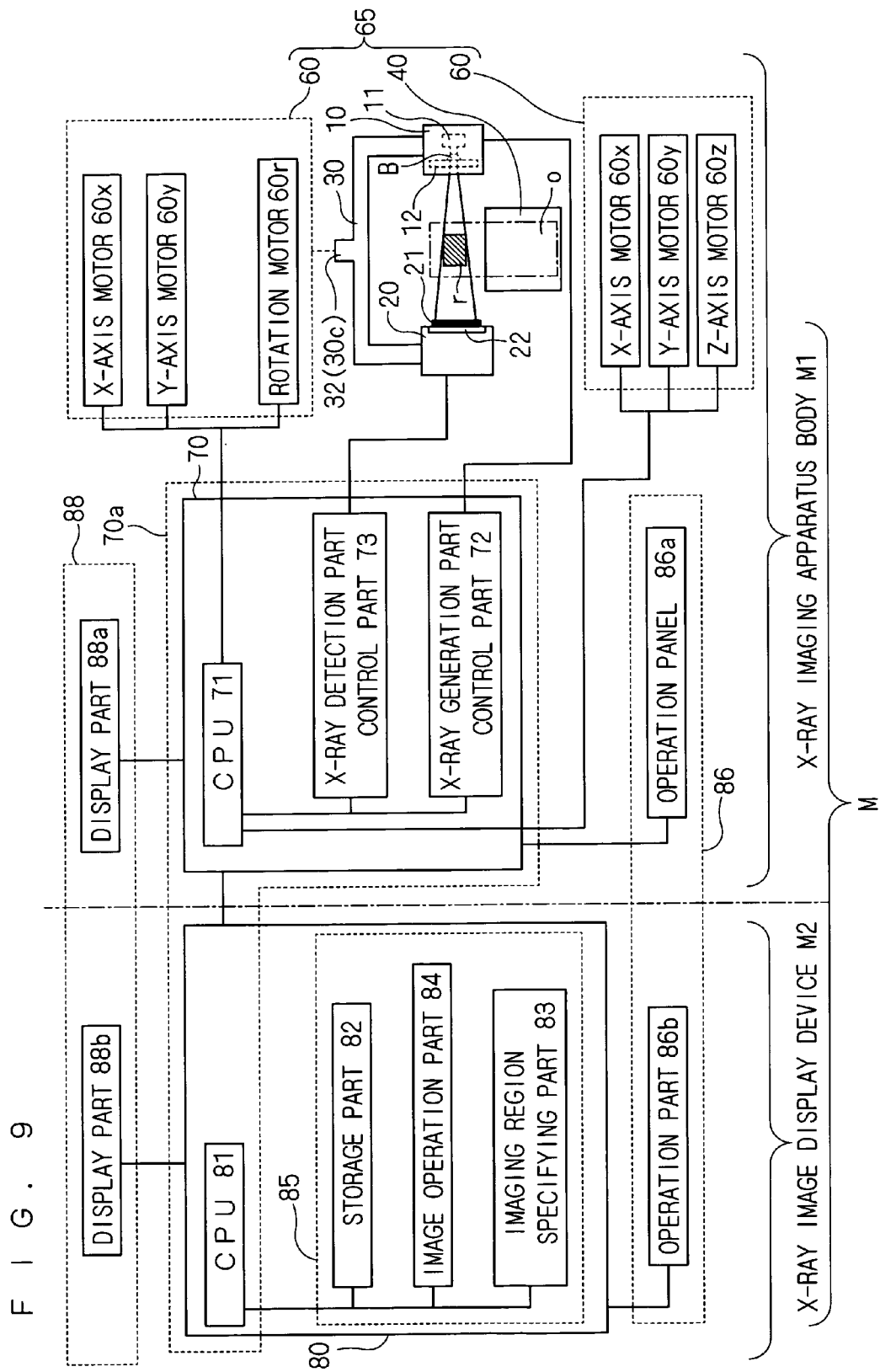

Further, FIG. 9 is a block diagram showing a medical X-ray CT imaging apparatus M different from the medical X-ray CT imaging apparatus M shown in FIG. 7. The medical X-ray CT imaging apparatus M of FIG. 9 has the same basic configuration as that of the medical X-ray CT imaging apparatus M of FIG. 7 but is different from the medical X-ray CT imaging apparatus M of FIG. 7 in that the X-ray imaging apparatus body M1 of FIG. 9 comprises another X-axis motor 60x and another Y-axis motor 60y which cooperate to horizontally move the subject holding part 40 and a Z-axis motor 60z for moving the subject holding part 40 up and down as well as the X-axis motor 60x and the Y-axis motor 60y which cooperate to horizontally move the axis 32 in order to relatively move the subject o held by the subject holding part 40 with respect to the supporting part 30 and the rotation motor 60r for rotating the supporting part 30. In FIGS. 7 to 9, the X-axis motor 60x, the Y-axis motor 60y, and the Z-axis motor 60z serve as an axis moving part to relatively move the axis 32 with respect to the subject o, and the rotation motor 60r serves as a rotation driving part to drive the supporting part 30 and the subject holding part 40 to rotate relative to each other. If the subject holding part 40 is rotated, however, the living body may possibly faint, and therefore, in most cases, a configuration wherein the supporting part 30 is rotated without rotating the subject holding part is adopted.

Thus, there are various possible mechanisms of the driving part 60 and the moving mechanism part 65 to relatively move the supporting part 30 with respect to the subject o. There may be a configuration wherein part of the X-axis motor 60x, the Y-axis motor 60y, and the Z-axis motor 60z is provided on the drive side of the supporting part 30 and the rest of those is provided on the drive side of the subject holding part 40, or there may be another configuration wherein at least part of the X-axis motor 60x, the Y-axis motor 60y, and the Z-axis motor 60z is provided on both the drive sides. The latter case has the advantage that it is possible to increase the amount of relative movement or increase the variety of movement patterns since the amounts of movement on both sides can be integrated. In terms of cost, however, the former configuration is preferable, wherein part of the X-axis motor 60x, the Y-axis motor 60y, and the Z-axis motor 60z is provided on the drive side of the supporting part 30 and the rest of those is provided on the drive side of the subject holding part 40 as shown in FIGS. 7 and 8.

More specifically, including the above exemplary configurations, first to sixth exemplary configurations described below can be adopted. The following first to sixth exemplary configurations can be applied to an x-ray imaging apparatus having such a configuration like the X-ray imaging apparatus body M1 as shown in FIG. 2.

In the first exemplary configuration, the X-axis motor 60x and the Y-axis motor 60y both for horizontally moving the axis 32, the rotation motor 60r for rotating the supporting part 30, and the Z-axis motor 60z for moving the supporting part 30 up and down are provided in the up-and-down moving frame 91 and no driving part for moving the subject holding part 40 is provided at the bottom of the fixed frame 90.

In the second exemplary configuration, the X-axis motor 60x and the Y-axis motor 60y both for horizontally moving the axis 32, and the rotation motor 60r for rotating the supporting part 30 are provided in the up-and-down moving frame 91 and the Z-axis motor 60z for moving the subject holding part 40 up and down is provided at the bottom of the fixed frame 90.

In the third exemplary configuration, the rotation motor 60r for rotating the supporting part 30 is provided in the up-and-down moving frame 91 and the X-axis motor 60x and the Y-axis motor 60y both for horizontally moving the subject holding part 40 and the Z-axis motor 60z for moving the subject holding part 40 up and down are provided at the bottom of the fixed frame 90.

In the fourth exemplary configuration, the rotation motor 60r for rotating the supporting part 30 and the Z-axis motor 60z for moving the supporting part 30 up and down are provided in the up-and-down moving frame 91 and the X-axis motor 60x and the Y-axis motor 60y both for horizontally moving the subject holding part 40 are provided at the bottom of the fixed frame 90.

In the fifth exemplary configuration, the rotation motor 60r for rotating the supporting part 30 and the Z-axis motor 60z for moving the supporting part 30 up and down are provided in the up-and-down moving frame 91, one of the X-axis motor 60x and the Y-axis motor 60y is provided in the up-and-down moving frame 91 to move the rotation axis 30c of the supporting part 30, and the other is provided at the bottom of the fixed frame 90 to move the subject holding part 40. Thus, the total motion of the X-axis motor 60x and the Y-axis motor 60y causes the X-ray generator 11 and the X-ray detector 21 to horizontally move with respect to the subject o.

In the sixth exemplary configuration, the rotation motor 60r for rotating the supporting part 30 is provided in the up-and-down moving frame 91, the Z-axis motor 60z for moving the subject holding part 40 up and down is provided at the bottom of the fixed frame 90, one of the X-axis motor 60x and the Y-axis motor 60y is provided in the up-and-down moving frame 91 to move the axis 32, and the other is provided at the bottom of the fixed frame 90 to move the subject holding part 40. Thus, the total motion of the X-axis motor 60x and the Y-axis motor 60y causes the X-ray generator 11 and the X-ray detector 21 to horizontally move with respect to the subject o.

The relative movement described in the present invention refers to a movement, like the relation between the subject o and the supporting part 30 shown in FIGS. 7 to 9 and the above-discussed first to sixth exemplary configurations, wherein as viewed from one a of these, the other β is seen to be moving, whether the one α is actually still or moving. Specifically, as viewed from the subject o, the supporting part 30 is moving. This includes a case where the subject o is still and the supporting part is moving, another case where the subject o is moving and the supporting part 30 is still, and still another case where both the subject o and the supporting part 30 are moving.

As the relative movement, there are various exemplary configurations other than those described above. The axis center of the axis 32 does not necessarily coincide with the center of rotation of an X-ray beam in imaging. The X-ray beam rotates, following the rotation of the supporting part 30, while being emitted. By combining the rotation of the supporting part 30 and the displacement of the axis 32, the center of rotation of the X-ray beam in imaging can be set at a portion different from the axis center of the axis 32. Japanese Patent Application Laid Open Gazette No. 2007-29168 applied by the present applicant discloses an exemplary configuration wherein the center of rotation of the X-ray beam in imaging is thus set, and in the present invention, CT imaging can be performed in such a manner. In the medical X-ray CT imaging apparatus M, a cone beam X-ray is generated from the X-ray source (the X-ray generator 11) to thereby perform CT imaging. In the CT imaging which uses a cone beam, the number of rotations of the supporting part 30 can be reduced, the load of the subject o can be reduced, and the whole apparatus can be downsized as compared with an imaging using a thin fan beam. Reconstruction requires only radiation data by a half rotation of the supporting part minimum. Panoramic radiography is performed by generating a long thin slit X-ray beam from the X-ray source (the X-ray generator 11) in a direction parallel to the rotation axis 30c. The change in the shape of the X-ray beam is made by using the slit or the collimator to limit the range of radiation of the X-ray emitted from the X-ray source. By controlling the slit or the collimator, the shape of an opening through which the X-ray passes is defined to a square, other rectangle, a circle, or the like, whereby a cone beams is emitted, or the shape of the opening is defined to a long thin slit parallel to the rotation axis 30c, whereby a slit X-ray beam is emitted. In terms of cost, preferable is a configuration wherein switching between the radiation of a cone beam X-ray and the radiation of a slit X-ray beam can be made by controlling the slit or the collimator provided on the front of a single X-ray source. There may be a case where the X-ray detector 21 for CT imaging and that for panoramic radiography is switched therebetween, or there may be another case where a region for X-ray radiation to the detection surface of a single X-ray detector 21 is switched between for CT imaging and for panoramic radiography. As an exemplary case where the X-ray detector 21 for CT imaging and that for panoramic radiography is switched therebetween, there is a configuration wherein a plurality of types of cassettes 22 shown in FIGS. 7 to 9 are prepared for CT imaging and for panoramic radiography and these cassettes 22 are replaced with one another. As an exemplary case where the region for X-ray radiation to the detection surface of a single X-ray detector 21 is switched between for CT imaging and for panoramic radiography, there is a configuration wherein the X-ray is emitted to the entire detection surface of the X-ray detector for CT imaging and X-ray is emitted to a long thin slit portion for panoramic radiography in the direction parallel to the rotation axis 30c at the center of the detection surface of the X-ray detector. Though the medical X-ray CT imaging apparatus M stands right from the floor on which the apparatus is set in the first preferred embodiment, a bed structure wherein imaging is performed on a patient lying thereon may be adopted and the inclination of the rotation axis 30c may be given arbitrarily. As an X-ray sensor serving as the X-ray detector, for example, a CCD sensor, a MOS sensor, a CMOS sensor, a TFT sensor, an FT sensor, a sensor consisting of X-ray solid-state image pickup elements, an image intensifier, or the like may be adopted only if it has a two-dimensionally detection surface.

In the first preferred embodiment, by using the medical X-ray CT imaging apparatus M having the above-described configuration, the imaging regions r of living organs (for example, bilaterally symmetrical temporomandibular joints or an upper tooth row and a lower tooth row which are vertically symmetrical) which are symmetrically located with respect to a predetermined plane are specified by the operation part 86 and the like and X-ray CT imaging is consecutively performed mainly on the respective imaging regions r of the living organs. Hereinafter, discussion will be made on a specific case where CT imaging is performed on temporomandibular joints. One of the living organs symmetrically located is defined as a first living organ and the other is defined as a second living organ.

Figure 10:
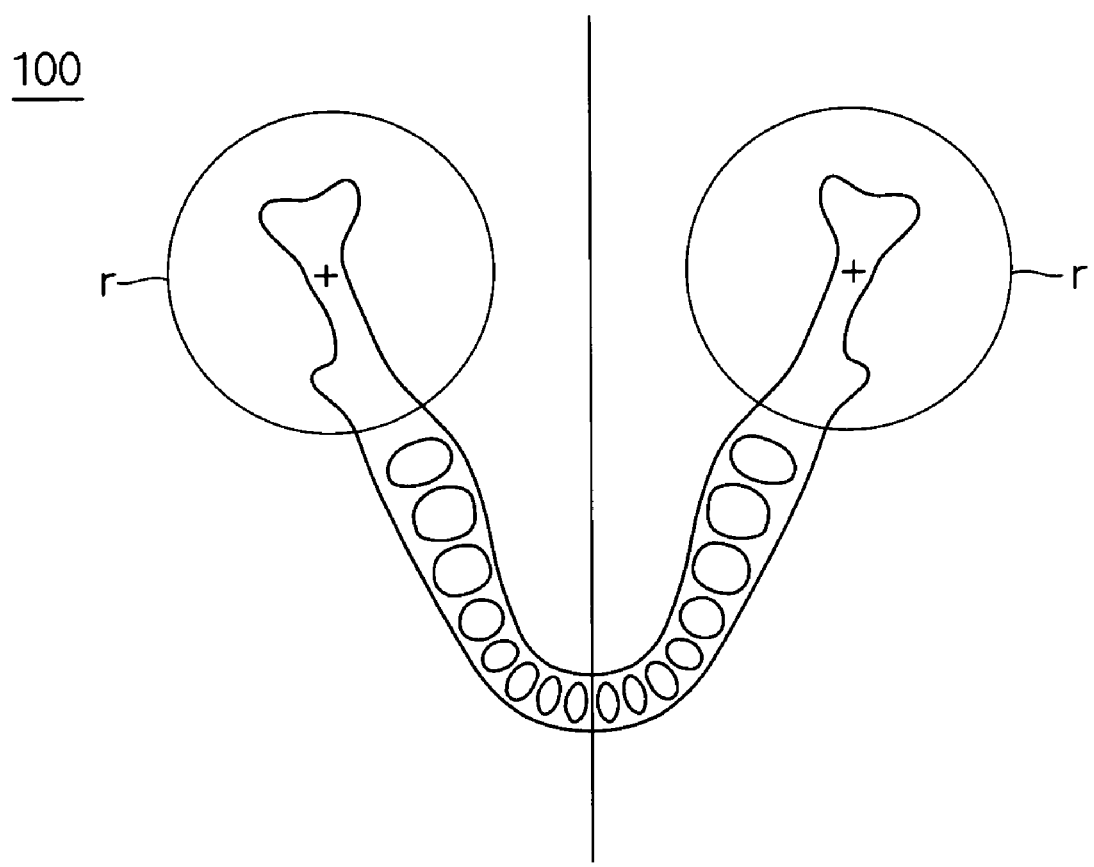
FIG. 10 is an illustration of a dental arch displayed by the medical X-ray CT imaging apparatus M in accordance with the first preferred embodiment of the present invention.

First, such an illustration 100 of a dental arch as shown in FIG. 10 is displayed on the display part 88. The illustration to be displayed is not limited to such a two-dimensional one as shown in FIG. 10 but may be a three-dimensional one. As an exemplary three-dimensional display, as seen in so-called computer graphics, three-dimensional image data of a stereoscopic dental arch of upper and lower teeth is generated and for example, the data is perspectively displayed or rotationally displayed by an additional operation. Observing the display part 88 on which the dental arch is displayed as shown in FIG. 10, the operator specifies the positions of the temporomandibular joints by using the operation part 86 to determine the imaging region r. As to the specification of the positions of the temporomandibular joints, there may be a manner where the position of either one (for example, the right temporomandibular joint) is specified and the position of the other is automatically calculated, or the positions of both temporomandibular joints may be specified. Though the imaging regions r are represented by circles on the illustration 100 in FIG. 10, other representations may be adopted, for example, where the center of the imaging region r is represented by a cross, or the like. In the case where the illustration is three-dimensional, the imaging region r is three-dimensionally represented by a translucent sphere, a cylinder, or the like.

After the imaging regions r are specified as shown in FIG. 10, the imaging region specifying part 83 or the like calculates the coordinates of the imaging region r and the CPU 71 uses the driving part 60 to drive the supporting part 30 and the subject holding part 40 on the basis of the calculated coordinates. Specifically, for example, the supporting part 30 and the subject holding part 40 are two-dimensionally moved by the XY table 62 or 64 and when the supporting part 30 and the subject holding part 40 reach the target positions, the supporting part 30 is rotated by the rotation motor 60r and CT imaging is performed on the right-side imaging region r (temporomandibular joint) shown in FIG. 10. Subsequently, the supporting part 30 and the subject holding part 40 are two-dimensionally moved by the XY table 62 or 64 and when the supporting part 30 and the subject holding part 40 reach the target positions, the supporting part 30 is rotated by the rotation motor 60r and CT imaging is automatically and consecutively performed on the left-side imaging region r (temporomandibular joint) shown in FIG. 10. In other words, the local CT imaging is automatically and consecutively performed on the right-side imaging region r (temporomandibular joint) shown in FIG. 10 and the left-side imaging region r (temporomandibular joint) shown in FIG. 10. The panoramic radiography of the dental arch may be performed while the local CT imaging is performed on the temporomandibular joints.

The image for region specification which is displayed on the display part 88 may be an image wherein the subject is illustrated, like the illustration 100 of the dental arch shown in FIG. 10, or an image obtained by actually imaging the subject with a camera for capturing normal visible light, instead of the illustration, only if the position has been set appropriately.

Figure 11:
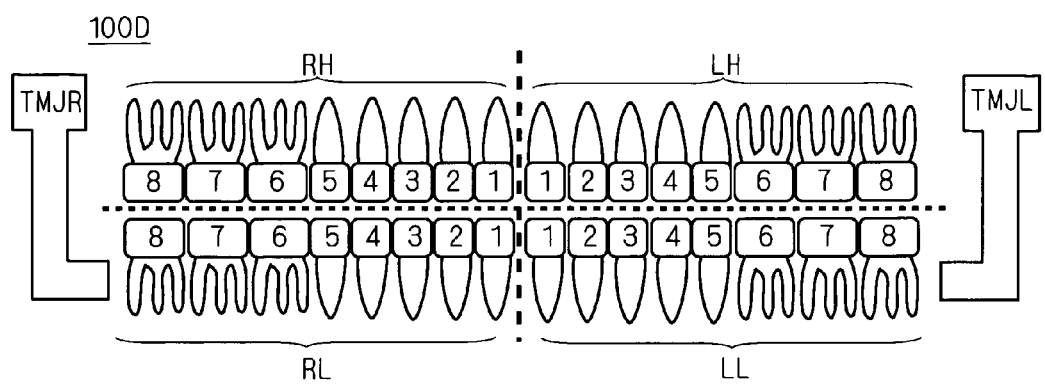
FIGS. 11 and 12 are views showing an exemplary image for region specification.
Figure 12:
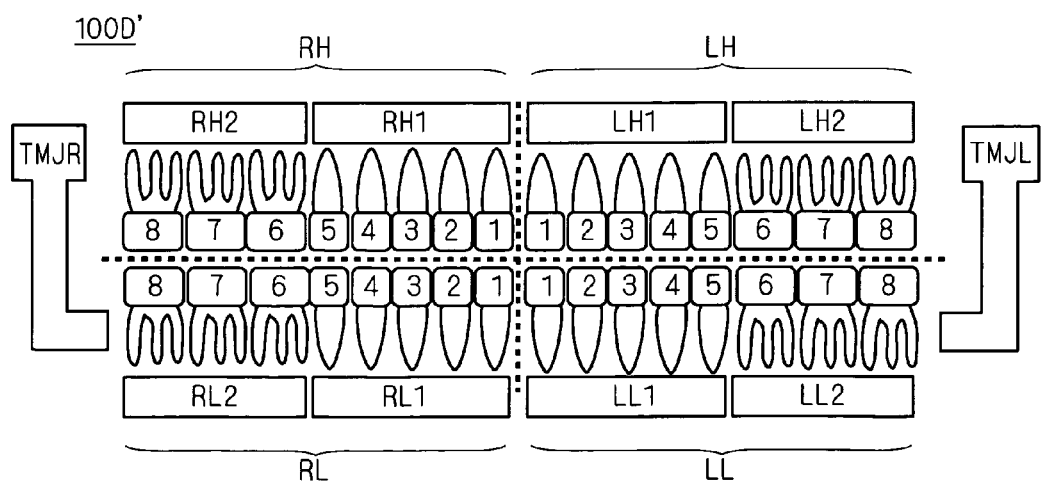

An actual shape is not necessarily required to be displayed and an image like a schematic illustration 100D as shown in FIGS. 11 and 12 may be displayed.

In FIG. 11, a series of teeth on the right side of the upper jaw, ranging from the front tooth to the molar, is defined as an RH group including the first to eighth teeth, and a series of teeth on the left side of the upper jaw, ranging from the front tooth to the molar, is defined as an LH group including the first to eighth teeth. A series of teeth on the right side of the lower jaw, ranging from the front tooth to the molar, is defined as an RL group including the first to eighth teeth, and a series of teeth on the left side of the lower jaw, ranging from the front tooth to the molar, is defined as an LL group including the first to eighth teeth.

In FIG. 11, "TMJR" represents a right-side temporomandibular joint and "TMJL" represents a left-side temporomandibular joint. The RL group and the LL group are symmetrical to the RH group and the LH group with respect to the occlusal surface, and the LH group and the LL group are symmetrical to the RH group and the RL group with respect to a plane including the median line. TMJR and TMJL are symmetrical to each other with respect to the plane including the median line.

Herein, "the plane including the median line" refers to a plane for symmetrically dividing a head into left and right sides or a plane for symmetrically dividing a whole body into left and right sides. The "symmetrical relation with respect to the occlusal surface" and the "symmetrical relation with respect to the plane including the median line" are examples of "symmetry" in the present invention.

For specifying a portion, there may be a configuration, for example, wherein a touch panel is used as the display part 88 and the portion is specified by touching the touch panel. There may be another configuration which is well known in the field of computer, wherein the portion is specified by using a mouse or the like to move a pointer displayed on the screen of the display part 88, or still another configuration wherein the portion is specified by using a keyboard to input the number displayed in the image, such as "RH8" in the case where the first tooth on the upper right is intended to be specified.

In such a case, when the left and right portions are defined as a pair of the first living organ and the second living organ, there may be a manner where when the eighth tooth in the RH group is specified, for example, the eighth tooth in the LH group is also automatically specified. When the upper and lower portions are defined as a pair of the first living organ and the second living organ, there may be a manner where when the eighth tooth in the RH group is specified, for example, the eighth tooth in the RL group is also automatically specified.

Thus, in the case of left and right symmetrical pair, for example, when the eighth tooth in the RH group and the eighth tooth in the LH group are specified, CT imaging is performed consecutively on the portion corresponding to the eighth tooth in the RH group and the portion corresponding to the eighth tooth in the LH group.

In the case of upper and lower symmetrical pair, when the eighth tooth in the RH group and the eighth tooth in the RL group are specified, CT imaging is performed consecutively on the portion corresponding to the eighth tooth in the RH group and the portion corresponding to the eighth tooth in the RL group.

Further, not only the specification of a specific one tooth but also a range specification may be made.

In the case where a touch panel is used as the display part 88, for example, by moving a finger to touch a range from one tooth to another tooth, such a control is made as to capture the image of the teeth in this range by CT imaging.

In such a case, when the left and right portions are defined as a pair of the first living organ and the second living organ, there may be a manner where when a range from the sixth tooth to the eighth tooth in the RH group are specified, for example, a range from the sixth tooth to the eighth tooth in the LH group are also automatically specified. When the upper and lower portions are defined as a pair of the first living organ and the second living organ, there may be a manner where when a range from the sixth tooth to the eighth tooth in the RH group are specified, for example, a range from the sixth tooth to the eighth tooth in the RL group are also automatically specified.

As to the range specification, as shown in FIG. 12, for example, there may be a manner where the whole is sectioned by zones to perform a zone specification. In the illustrated case, in a schematic image like the illustration 100D' similar to the illustration 100D of FIG. 11, zone sectioning is made where the zone near the front tooth, including the first to fifth teeth in the RH group, is represented as RH1 and the zone of the molars, including the sixth to eighth teeth in the RH group, is represented as RH2. Similarly, the zone near the front tooth, including the first to fifth teeth in the LH group, is represented as LH1 and the zone of the molars, including the sixth to eighth teeth in the LH group, is represented as LH2. The zone near the front tooth, including the first to fifth teeth in the RL group, is represented as RL1 and the zone of the molars, including the sixth to eighth teeth in the RL group, is represented as RL2. The zone near the front tooth, including the first to fifth teeth in the LL group, is represented as LL1 and the zone of the molars, including the sixth to eighth teeth in the LL group, is represented as LL2.

In the case where a touch panel is used as the display part 88, for example, when a frame represented by "RH2" shown in FIG. 12 is touched, the range containing the sixth to eighth teeth in the zone RH2 is specified to be captured by CT imaging.

In such a case, when the left and right portions are defined as a pair of the first living organ and the second living organ, there may be a manner where when the zone RH2 is specified, for example, the zone LH2 is also automatically specified. When the upper and lower portions are defined as a pair of the first living organ and the second living organ, there may be a manner where when the zone RH2 is specified, for example, the zone RL2 is also automatically specified.

Thus, in the case of left and right symmetrical pair, for example, when the sixth to eighth teeth in the RH group and the sixth to eighth teeth in the LH group are specified, CT imaging is performed consecutively on the portion corresponding to the sixth to eighth teeth in the RH group and the portion corresponding to the sixth to eighth teeth in the LH group.

In the case of upper and lower symmetrical pair, when the sixth to eighth teeth in the RH group and the sixth to eighth teeth in the RL group are specified, CT imaging is performed consecutively on the portion corresponding to the sixth to eighth tooth in the RH group and the portion corresponding to the sixth to eighth tooth in the RL group.

The RH group, the LH group, the RL group, or the LL group may be simply specified. As such an example, in the case where a touch panel is used as the display part 88, when a frame represented by "RH" shown in FIGS. 11 and 12 is touched, the range containing all the first to eighth teeth in the RH group is specified to be captured by CT imaging. In such a case, when the left and right portions are defined as a pair of the first living organ and the second living organ, there may be a manner where when the RH group is specified, the LH group is also automatically specified. When the upper and lower portions are defined as a pair of the first living organ and the second living organ, there may be a manner where when the RH group is specified, the RL group is also automatically specified.

Thus, in the case of left and right symmetrical pair, for example, when the RH group and the LH group are specified, CT imaging is performed consecutively on the portion corresponding to the RH group and the portion corresponding to the LH group.

In the case of upper and lower symmetrical pair, for example, when the RH group and the RL group are specified, CT imaging is performed consecutively on the portion corresponding to the RH group and the portion corresponding to the RL group.

There may be a case where a frame is prepared in advance and a desired range is specified by moving the frame on the display part 88 so that the frame can contain the desired range.

As another example, an image obtained by radiography of the subject may be used as the image for region specification which is displayed on the display part 88.

Specifically, as discussed later, there may be a case where a panoramic image obtained by capturing the subject through panoramic radiography is displayed like a panoramic image 200 shown in FIG. 13 and used for specifying a position, or another case where transmitted images of the subject o are obtained from different angles prior to CT imaging, the transmitted image obtained from each angle is displayed, a target position is specified on the displayed transmitted image, and CT imaging is performed on the target portion.

Though the case where the schematic illustration is displayed has been discussed with reference to FIGS. 11 and 12, there may be a case where a plurality of buttons are provided in three-dimensional shape and arrangement of the illustration, to specify a position. This is an exemplary case for directly specifying the portion without displaying the image for region specification on the screen.

The above-discussed specifications by the tooth, by the range, by the sectioned group and the like can be applied to other preferred embodiments. For example, by overlapping an enclosing line representing the above zone on the illustration 100 in FIG. 10, or by displaying the enclosing line near the zone, the specification manners can be applied as appropriate.

Next, electrical signals (data) obtained by the X-ray detector 21 through the CT imaging are reconstructed by the image operation part 84 as CT images and the CT images are displayed on the display part 88. FIG. 13 shows a display example of the screen displayed on the display part 88. In a display screen 2 shown in FIG. 13, the panoramic image 200 of a dental arch X including the temporomandibular joints and a CT cross sectional image 201 of the temporomandibular joints are displayed at an upper part and a lower part for comparison. The CT cross sectional image 201 includes an image 2010 showing a right-side temporomandibular joint YR in the closed state, an image 2011 showing a left-side temporomandibular joint YL in the closed state, an image 2012 showing a right-side temporomandibular joint yR in the open state, and an image 2013 showing a left-side temporomandibular joint yL in the open state. In order to obtain the CT images representing the temporomandibular joints YR and YL in the closed state and the temporomandibular joints yR and yL in the open state which are shown in FIG. 13, the above-discussed local CT imaging needs to be performed twice in the open state and the closed state.

Thus, in order to conduct a diagnosis on living organs symmetrically located with respect to a predetermined plane, CT imaging needs to be performed on each of the living organs, and this requires a complicated operation wherein the operator positions one of the living organs and performs CT imaging thereon, and after that, the operator positions the other and performs CT imaging thereon. The medical X-ray CT imaging apparatus M of the first preferred embodiment, however, specifies the imaging regions r of both the living organs and thereafter automatically and consecutively performs the local CT imaging on both the imaging regions r, and therefore the load of the operator can be reduced. Further, the medical X-ray CT imaging apparatus M of the first preferred embodiment can be configured to perform local CT imaging on only part of the subject o as the imaging region, and in this case, it is possible to perform X-ray CT imaging on the living organs with high resolution and less radiation exposure dose. Furthermore, since the medical X-ray CT imaging apparatus M of the first preferred embodiment performs local X-ray CT imaging, the apparatus occupies only the same area as that of the conventional dental panoramic radiography apparatus and can be housed in an X-ray proof chamber of a dental clinic or the like.

The Second Preferred Embodiment

A medical X-ray CT imaging apparatus M of the second preferred embodiment changes the imaging condition on the basis of whether the subject o is an adult or a child. With reference to the flowchart of FIG. 14, an operation of the medical X-ray CT imaging apparatus M of the second preferred embodiment will be discussed. The configuration of the medical X-ray CT imaging apparatus M of the second preferred embodiment is the same as that of the medical X-ray CT imaging apparatus M of the first preferred embodiment, and therefore detailed description thereof will be omitted.

First, in Step S1 of FIG. 14, the subject o is positioned at the X-ray CT imaging apparatus. Specifically, in Step S1, the subject o is held by the subject holding part 40. In Step S2, it is checked whether the size of adult is selected or not by the operation part 86 as the size of the subject o. If Yes in Step S2, the process goes to Step S3, and if No, the process goes to Step S4. In Step S3, in accordance with the selection of the size of adult as the size of the subject o, the imaging condition for adult is set. The size of the living organ of an adult is different from that of the living organ of a child, and therefore it is desirable that the imaging is performed under the imaging condition for adult. Specifically, as the imaging condition to change the size of the imaging region r, the width of the slit of the radiation field control part 12 for controlling the range of the X-ray beam emitted from the X-ray source may be changed or the enlargement ratio may be changed by using the moving mechanism part to change the positional relation between the subject o and the X-ray generator 11. Since the enlargement ratio is usually represented by the ratio of the distance between the subject and the X-ray detector to the distance between the X-ray source and the X-ray detector, the ratio has only to be changed. By controlling the tube voltage, the tube current, the irradiation time, and the rotation speed, the X-ray radiation dose may be changed, for example, reduced for a child as compared with the case for an adult. The change in the width of the slit and the change in the enlargement ratio may be combined. The size of the imaging region r is changed not only depending on whether the subject is an adult or a child but also in accordance with the type of living organ to be imaged. For example, the size of the imaging region r is changed between when the imaging target is an auditory ossicle and when the imaging target is a cochlea. The size of the imaging region r is changed by an imaging region changing part constituted of the X-ray generation part control part 72 and the X-ray detection part control part 73.

In Step S4, it is checked whether the size of child is selected or not by the operation part 86 as the size of the subject o. If Yes in Step S4, the process goes to Step S5, and if No, the process goes back to Step S2. In Step S5, in accordance with the selection of the size of child as the size of the subject o, the imaging condition for child is set.

Next, in Step S6, it is checked whether a CT imaging mode is selected or not by the operation part 86. In Yes in Step S6, the process goes to Step S7, and if No, the process goes to Step S8. In Step S7, it is checked whether a temporomandibular joint imaging mode is selected or not. If Yes, the process goes to Step S9, and if No, the process goes to Step S17. The temporomandibular joint imaging mode in Step S7 refers to a mode for consecutively performing CT imaging on the left and right temporomandibular joints. Step S17 is a normal routine for CT imaging, in other words, a process wherein serial imaging is not particularly performed and CT imaging such as local CT imaging of a desired portion is performed once for one position specification. Since this is well-known CT imaging which is performed by relatively positioning the supporting part with respect to the subject and rotating the supporting part, detailed discussion on the process steps will be omitted. Since the normal CT imaging refers to imaging which is not performed serially, this does not exclude the CT imaging of either one of the left and right temporomandibular joints, which is performed once for one position specification. In Step S9, the temporomandibular joint is specified as the imaging region r. As discussed in the first preferred embodiment, as the specification manner, one or both of the temporomandibular joints may be specified by the operation part 86 with the illustration thereof or the like or may be specified on the basis of data set in advance. The portion may be specified directly by using the operation part 86 to input the name of the portion or code thereof without displaying any image on the screen, as discussed earlier.

Next, in Step S10, on the basis of the imaging region r specified in Step S9, CT imaging is performed on either one of the left and right temporomandibular joints. Then, in Step S11, CT imaging is performed on the rest of the left and right ones. In Step S12, CT images are reconstructed on the basis of the electrical signals (left and right temporomandibular joint data) captured in Steps S10 and S11. In Step S13, the CT images of the left and right temporomandibular joints which are reconstructed in Step S12 are displayed on the display part 88 (display device).

On the other hand, in Step S8, it is checked whether panoramic radiography is selected or not by the operation part 86. In Yes in Step S8, the process goes to Step S14, and if No, the process goes back to Step S6. In Step S14, panoramic radiography is performed, and in Step S15, panoramic images are reconstructed on the basis of the electrical signals (panoramic data) captured in Step S14. Then, in Step S16, the panoramic images reconstructed in Step S15 are displayed on the display part 88 (display device). Herein, mention will be made on the position control in the CT imaging on one temporomandibular joint and the other temporomandibular joint performed in Steps S9 to S11. If the subject to be imaged is a living body having normal and general physique and skeleton, the positions in the three-dimensional space where the X-ray imaging apparatus body M1 is provided, where one of the paired organs is located and other is located, may be set in advance as coordinate data. By utilizing this, it is possible to control the moving mechanism part 65 to perform CT imaging of the region and therearound on the basis of the coordinate data. For example, if a key for "right temporomandibular joint" is prepared, since the control of the moving mechanism part 65 to perform local CT imaging of the region of the right temporomandibular joint in the three-dimensional space, which would be present if the subject has normal and general physique and skeleton, can be set only by turning the key ON without any input of specific three-dimensional coordinates by the operator, it is possible to perform CT imaging of the right temporomandibular joint by one-touch operation only if the subject o is fixed to the subject holding part 40. Since similar three-dimensional control can be made as to the left temporomandibular joint, it is possible to consecutively perform CT imaging of one temporomandibular joint and the other temporomandibular joint only by specifying one temporomandibular joint. The same applies to other organs as well as the temporomandibular joints.

By making setting so that the region displayed in the illustration 100 should coincide with the position of the region in the three-dimensional space where the X-ray imaging apparatus body M1 is provided, it is possible to perform CT imaging of a desired region. Thus, the region specification on the illustration can be converted into the specification of the region in the three-dimensional space for the subject o fixed to the subject holding part 40. As a matter of course, instead of the data on the normal and general physique and skeleton, data on physiques and skeletons of individual living bodies may be prepared and used. As discussed earlier, without displaying any image for region specification, like the illustration 100 of FIG. 10, on the screen, the portion may be specified directly by using the operation part 86 to input the name of the portion or code thereof. This can be achieved on the basis of the above-discussed coordinate data. There may be a configuration, for example, wherein a key for starting execution of serial imaging of the temporomandibular joints is set, such as a key of a keyboard or a key displayed on the screen to be clicked by a mouse, and after the operation comes into the temporomandibular joint imaging mode, the key for starting execution of serial imaging of the temporomandibular joints is turned ON. There may be another configuration wherein panoramic radiography is first performed prior to CT imaging, the obtained panoramic image is displayed, a target portion is specified on the displayed panoramic image, and CT imaging is thereby performed on the target portion, and also to this case, the above principle can be applied. An example of such a configuration is disclosed in Republication WO 2003/0834407 which is applied by the present applicant. In the panoramic radiography, a panoramic section which is a thin layer of substantial horseshoe shape is assumed to exist in the three-dimensional space where the X-ray imaging apparatus body M1 is provided and panoramic radiography is set to capture the panoramic section. Since the displayed panoramic image is obtained by developing the panoramic section, it is possible to determine the position in the three-dimensional space by specifying a specific position on the panoramic image. There may be a manner where the panoramic image is first displayed by utilizing this and the temporomandibular joints are specified on the displayed panoramic image. Such a panoramic image as discussed above, which is used for position specification, is referred to as a panoramic scout view. In FIG. 13, an image used for such a panoramic scout view may be displayed as the panoramic image 200.

Further, a configuration can be adopted, wherein transmitted images of the subject o are obtained from different angles prior to the CT imaging, the transmitted images obtained from the different angles are displayed, a target position is specified on the displayed transmitted images, and the CT imaging is performed on the target portion, and also to this case, the above principle can be applied. An example of such a configuration is disclosed in Japanese Patent Application Laid Open Gazette No. 2004-329293 which is applied by the present applicant. If the positions in a direction parallel to the axial direction of the rotation axis 30c are the same in a plurality of transmitted images, by specifying the position in a direction intersecting the axial direction of the rotation axis 30c, the position in the three-dimensional space can be specified. By utilizing this, there may be a case where a plurality of transmitted images obtained from different angles are displayed and the temporomandibular joints are specified on the displayed transmitted images. As discussed above, such a transmitted image as discussed above, which is used for position specification, is referred to as a two-directional transmitted image scout view. In FIG. 13, an image used as the two-directional transmitted image scout view may be displayed, instead of the panoramic image 200. The above-described examples such as panoramic scout view and two-directional transmitted image scout view allow more accurate position specification since the views are based on the data obtained by capturing the image of an individual living body.

With reference to the flowchart of FIG. 14, the operation of the medical X-ray CT imaging apparatus M for performing the CT imaging on the temporomandibular joints in the open or closed state has been discussed. Now, with reference to the flowchart of FIG. 15, an operation of the medical X-ray CT imaging apparatus M for performing the CT imaging on the temporomandibular joints in the open and closed states will be discussed. The flowchart of FIG. 15 is basically the same as that of FIG. 14 and the same process steps are represented by the same reference sign and detailed description thereof will be omitted.

In Step S10a, CT imaging is performed on one of the left and right temporomandibular joints in the open state on the basis of the imaging region r specified in Step S9. In Step S11a, CT imaging is performed on the other temporomandibular joint in the open state. In Step S10b, CT imaging is performed on one of the left and right temporomandibular joints in the closed state on the basis of the imaging region r specified in Step S9. In Step S11b, CT imaging is performed on the other temporomandibular joint in the closed state. In Step S12a, CT images are reconstructed on the basis of the electrical signals (the left and right temporomandibular joint data in the open state) captured in Steps S10a and 11a and the electrical signals (the left and right temporomandibular joint data in the close state) captured in Steps S10b and S11b. In Step S13a, the CT images of the left and right temporomandibular joints in the open and closed states which are reconstructed in Step S12a are displayed on the display part 88 (display device).

Figure 16:
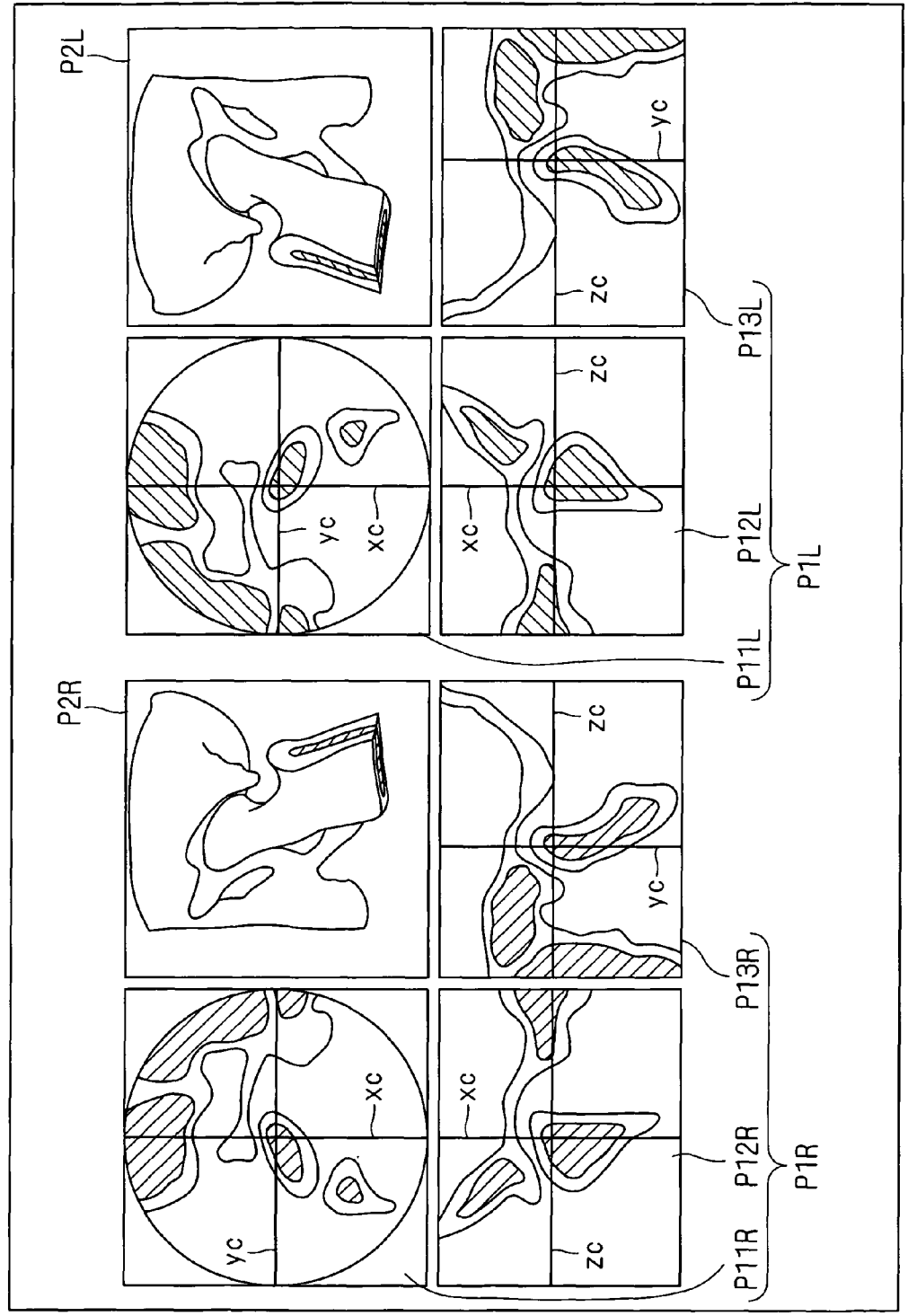
FIGS. 16 and 17 are views showing a display screen of the medical X-ray CT imaging apparatus M in accordance with the second preferred embodiment of the present invention.

FIG. 16 shows the CT images of the temporomandibular joints in the closed state which are displayed on the display part 88 in Step S13 of FIG. 14. In the CT images shown in FIG. 16, a cross sectional CT image P1R of the right-side temporomandibular joint of the subject o and a volume rendering image P2R of the right-side temporomandibular joint are displayed on the left side of the screen and a cross sectional CT image P1L of the left-side temporomandibular joint of the subject o and a volume rendering image P2L of the left-side temporomandibular joint are displayed on the right side of the screen. The cross sectional CT image P1R includes a cross sectional CT image P11R of the right-side temporomandibular joint sectioned by an xy plane which is shown in the upper left, a cross sectional CT image P12R of the right-side temporomandibular joint sectioned by an xz plane which is shown in the lower left, and a cross sectional CT image P13R of the right-side temporomandibular joint sectioned by a yz plane which is shown in the lower right. Similarly, the cross sectional CT image P1L includes a cross sectional CT image P11L of the left-side temporomandibular joint sectioned by the xy plane which is shown in the upper left, a cross sectional CT image P12L of the left-side temporomandibular joint sectioned by then xz plane which is shown in the lower left, and a cross sectional CT image P13L of the left-side temporomandibular joint sectioned by the yz plane which is shown in the lower right.

In the CT imaging, since the position of an imaging target portion, i.e., each temporomandibular joint in this case, can be detected, a default cross section displayed first in each of the cross sectional CT images can be set, for example, near the center of the portion. In the figure, the cross section of each cross sectional CT image is set centering the center of a caput mandibulae and therearound of each temporomandibular joint. As discussed below, the position of the cross section can be moved by, for example, cursors zc, yc, and xc, or the like.

The two-dimensional plane consisting of y and z in an x coordinate is defined as the yz plane, the two-dimensional plane consisting of x and z in a y coordinate is defined as the xz plane, and the two-dimensional plane consisting of x and y in a z coordinate is defined as the xy plane. The xy plane, the xz plane, and the yz plane are cross sections orthogonal to one another. A z cursor zc indicating a position of the xy plane is shown in the xz plane and the yz plane, a y cursor yc indicating a position of the xz plane is shown in the xy plane and the yz plane, and an x cursor xc indicating a position of the yz plane is shown in the xy plane and the xz plane. The cursors zc, yc, and xc are moved by an operation of a pointer with a mouse, to thereby move the respective positions of the xy plane, the xz plane, and the yz plane.

The x cursor xc in the xy plane and the x cursor xc in the xz plane are interlocked, and when one of the cursors is moved, the other is automatically moved. The y cursor yc in the xy plane and the y cursor yc in the yz plane are in the same relation, and the z cursor zc in the xz plane and the z cursor zc in the yz plane are also in the same relation.

Figure 17:
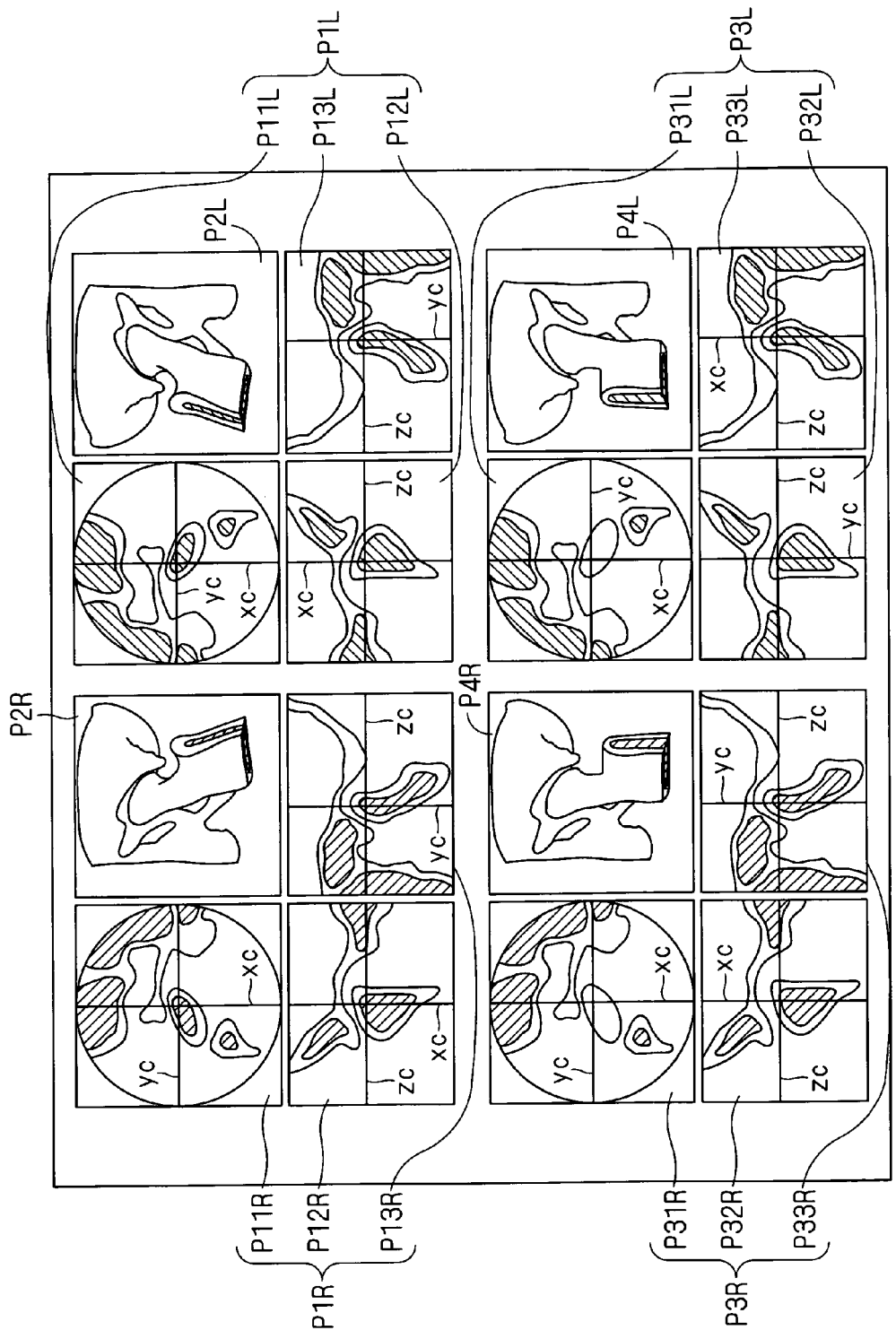

On the other hand, FIG. 17 shows the CT images of the temporomandibular joints in the closed and open states which are displayed on the display part 88 in Step S13*a* of FIG. 15. In the CT images shown in FIG. 17, the CT images of the closed state are displayed on the upper stage of the screen, and the CT images of the open state are displayed on the lower stage of the screen. The CT images on the upper stage of FIG. 17 are the same as the CT images shown in FIG. 16. The cross sectional CT image P1R of the right-side temporomandibular joint in the closed state and the volume rendering image P2R of the right-side temporomandibular joint are displayed on the left side of the screen. The cross sectional CT image P1L of the left-side temporomandibular joint in the closed state and the volume rendering image P2L of the left-side temporomandibular joint are displayed on the right side of the screen. In the CT images on the lower stage of FIG. 17, a cross sectional CT image P3R of the right-side temporomandibular joint in the open state and a volume rendering image P4R of the right-side temporomandibular joint are displayed on the left side of the screen, and a cross sectional CT image P3L of the left-side temporomandibular joint in the open state and a volume rendering image P4L of the left-side temporomandibular joint are displayed on the right side of the screen. The cross sectional CT image P3R includes a cross sectional CT image P31R of the right-side temporomandibular joint in the open state sectioned by the xy plane which is shown in the upper left, a cross sectional CT image P32R of the right-side temporomandibular joint in the open state sectioned by the xz plane which is shown in the lower left, and a cross sectional CT image P33R of the right-side temporomandibular joint in the open state sectioned by the yz plane which is shown in the lower right. Similarly, the cross sectional CT image P3L includes a cross sectional CT image P31L of the left-side temporomandibular joint in the open state sectioned by the xy plane which is shown in the upper left, a cross sectional CT image P32L of the left-side temporomandibular joint in the open state sectioned by the xz plane which is shown in the lower left, and a cross sectional CT image P33L of the left-side temporomandibular joint in the open state sectioned by the yz plane which is shown in the lower right.

Thus, since the medical X-ray CT imaging apparatus M of the second preferred embodiment performs the X-ray CT imaging of the temporomandibular joints in the open or closed state or the temporomandibular joints in the open and closed states while setting the adult size or the child size, it is possible to automatically control the X-ray radiation condition, such as the tube current and the tube voltage, of an optimal X-ray power supply, or the like, and possible for the apparatus to automatically determine roughly the center position of the imaging region r which is the position of the living organ (on the basis of the factory setting value) only by selecting adult or child.

Further, the medical X-ray CT imaging apparatus M of the second preferred embodiment performs the CT imaging on the temporomandibular joints in the closed and open states and reconstructs CT images on the basis of the data captured through the CT imaging. The medical X-ray CT imaging apparatus. M, however, performs the CT imaging on the temporomandibular joints in an intermediate state (between the closed and open states) at least once as well as the CT imaging on the temporomandibular joints in the closed and open states and reconstructs the CT images on the basis of the data captured through the CT imaging, to continuously reproduce the CT images. It is thereby possible to display the CT images of the temporomandibular joints from the open state to the closed state as a moving image on the display part 88.

Though the above discussion has been made on the case where the CT imaging is consecutively performed on the first living organ and the second living organ such as the left and right temporomandibular joints, the CT imaging may be performed not only on the first living organ and the second living organ but also mixedly on another portion.

Such another portion is referred to as a third living organ, which will be described with reference to FIG. 18.

Herein, the "third living organ" refers to a CT imaging target portion different from the first living organ and the second living organ and may be singular or plural.

Figure 18:
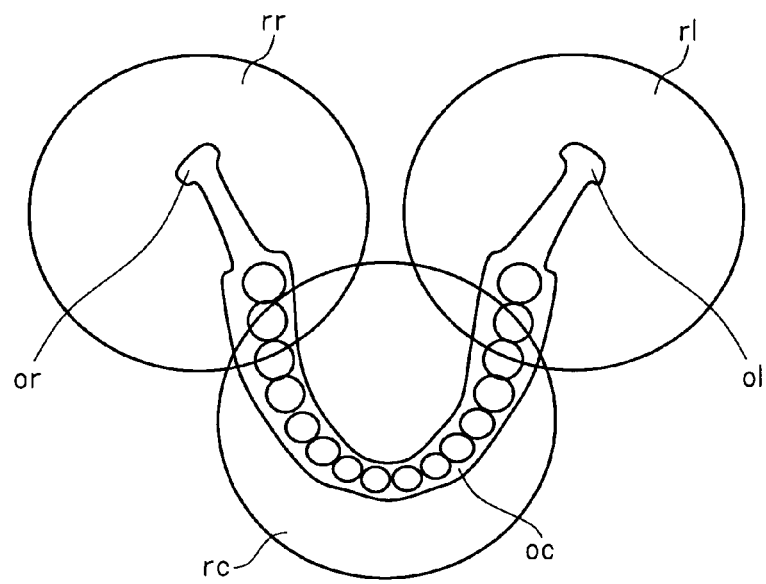
FIGS. 18 and 19 are views showing an exemplary case of setting an imaging region.

FIG. 18 shows an exemplary case where assuming that the right-side temporomandibular joint and portions in the vicinity thereof are defined as a right-side living organ or, the left-side temporomandibular joint and portions in the vicinity thereof are defined as a left-side living organ ol, and portions centering row of teeth between both the temporomandibular joints are defined as a central living organ oc, set are a right-side imaging region rr for the CT imaging of the right-side living organ or, a left-side imaging region rl for the CT imaging of the left-side living organ ol, and a central imaging region rc for the CT imaging of the central living organ oc.

In this exemplary case, the third living organ is a portion located between the first living organ and the second living organ and continuous with the first and second living organs.

The CT imaging is performed consecutively on the imaging region rr, the imaging region rl, and the imaging region rc, but the sequence is not limited to this.

Examples of the sequence are shown below.

Example 1: the CT imaging on the imaging region rr, the CT imaging on the imaging region rl, and the CT imaging on the imaging region rc, Example 2: the CT imaging on the imaging region rl, the CT imaging on the imaging region rr, and the CT imaging on the imaging region rc, Example 3: the CT imaging on the imaging region rc, the CT imaging on the imaging region rr, and the CT imaging on the imaging region rl, Example 4: the CT imaging on the imaging region rc, the CT imaging on the imaging region rl, and the CT imaging on the imaging region rr, Example 5: the CT imaging on the imaging region rr, the CT imaging on the imaging region rc, and the CT imaging on the imaging region rl, and Example 6: the CT imaging on the imaging region rl, the CT imaging on the imaging region rc, and the CT imaging on the imaging region rr.

Herein, it is assumed that one of the right-side living organ or and the left-side living organ ol is the first living organ, the other is the second living organ, and the central living organ oc is the third living organ.

In Examples 1 and 2, the CT imaging on the third living organ is performed after the serial CT imaging on the first living organ and the second living organ.

In Examples 3 and 4, the CT imaging on the third living organ is performed before the serial CT imaging on the first living organ and the second living organ.

In Examples 5 and 6, the CT imaging on the third living organ is performed between the serial CT imaging on the first living organ and the second living organ.

The sizes of the imaging region rr, the imaging region rl, and the imaging region rc are set so that the total size of the imaging region rr, the imaging region rl, and the imaging region rc may contain the entire dental arch including all of the upper jaw, the lower jaw, and the temporomandibular joints in width, depth, and height.

As shown in FIG. 18, the imaging region rc for the third living organ is located between the respective imaging regions rr and rl for the first and second living organs and is continuous with the imaging region rr and the imaging region rl. Since the three regions are continuous without any break, CT imaging data for the whole of the imaging target portions without any break can be obtained.

The imaging region rr, the imaging region rl, and the imaging region rc may be specified by the operator using the imaging region specifying part 83 as discussed earlier and may be positionally set if advance with respect to, for example, the position of the subject holding part.

The Third Preferred Embodiment

While discussion has been made on the configuration and operation of the medical X-ray CT imaging apparatus M in the above preferred embodiments, discussion will be made on display examples where the living organs symmetrically located with respect to a predetermined plane are displayed for comparison on the display part 88 of the medical X-ray CT imaging apparatus M in the third preferred embodiment.

Figure 20:
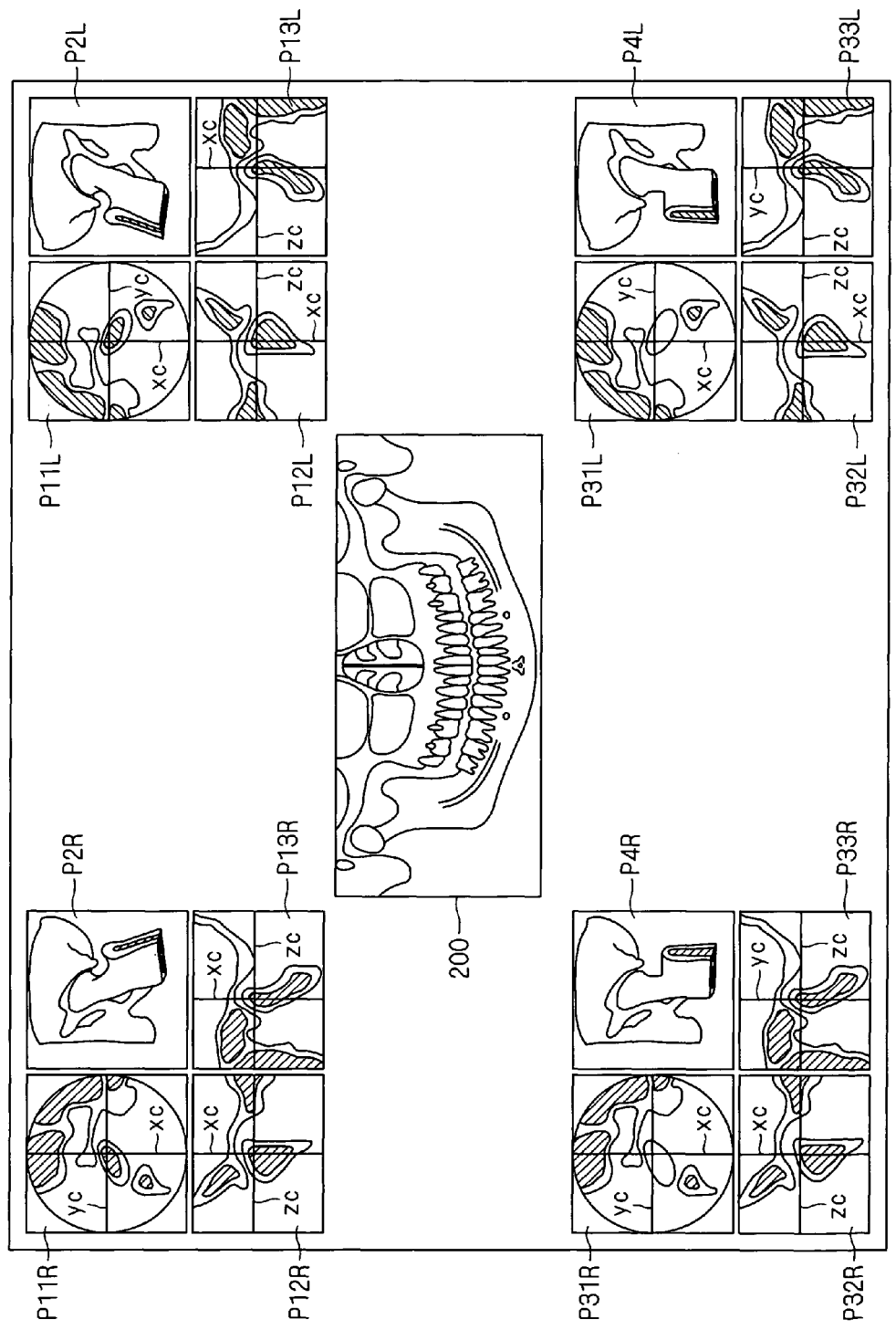
FIGS. 20 to 27 are views showing a display screen of the medical X-ray CT imaging apparatus M in accordance with a third preferred embodiment of the present invention.

In FIG. 20, first, shown is an exemplary case where the panoramic image 200 and the CT images of the temporomandibular joints in the closed and open states are displayed. In FIG. 20, the panoramic image 200 is displayed in the center and the CT images of the temporomandibular joints in the closed state are displayed on the upper stage and the CT images of the temporomandibular joints in the open state are displayed on the lower stage. Among the CT images on the upper stage of FIG. 20, the cross sectional CT images P11R to P13R of the right-side temporomandibular joint in the closed state and the volume rendering image P2R of the right-side temporomandibular joint are displayed on the left side of the screen, and the cross sectional CT images P11L to P13L of the left-side temporomandibular joint in the closed state and the volume rendering image P2L of the left-side temporomandibular joint are displayed on the right side of the screen. Among the CT images on the lower stage of FIG. 20, the cross sectional CT images P31R to P33R of the right-side temporomandibular joint in the open state and the volume rendering image P4R of the right-side temporomandibular joint are displayed on the left side of the screen, and the cross sectional CT images P31L to P33L of the left-side temporomandibular joint in the open state and the volume rendering image P4L of the left-side temporomandibular joint are displayed on the right side of the screen.

Thus, by displaying the panoramic image 200 and the CT images of the temporomandibular joints in the closed and open states for comparison, it is possible to examine the closed and open states of the temporomandibular joints while observing the entire dental arch including the temporomandibular joints in the panoramic image 200 and therefore possible to support efficient diagnoses and effective explanations for patients.

Figure 21:
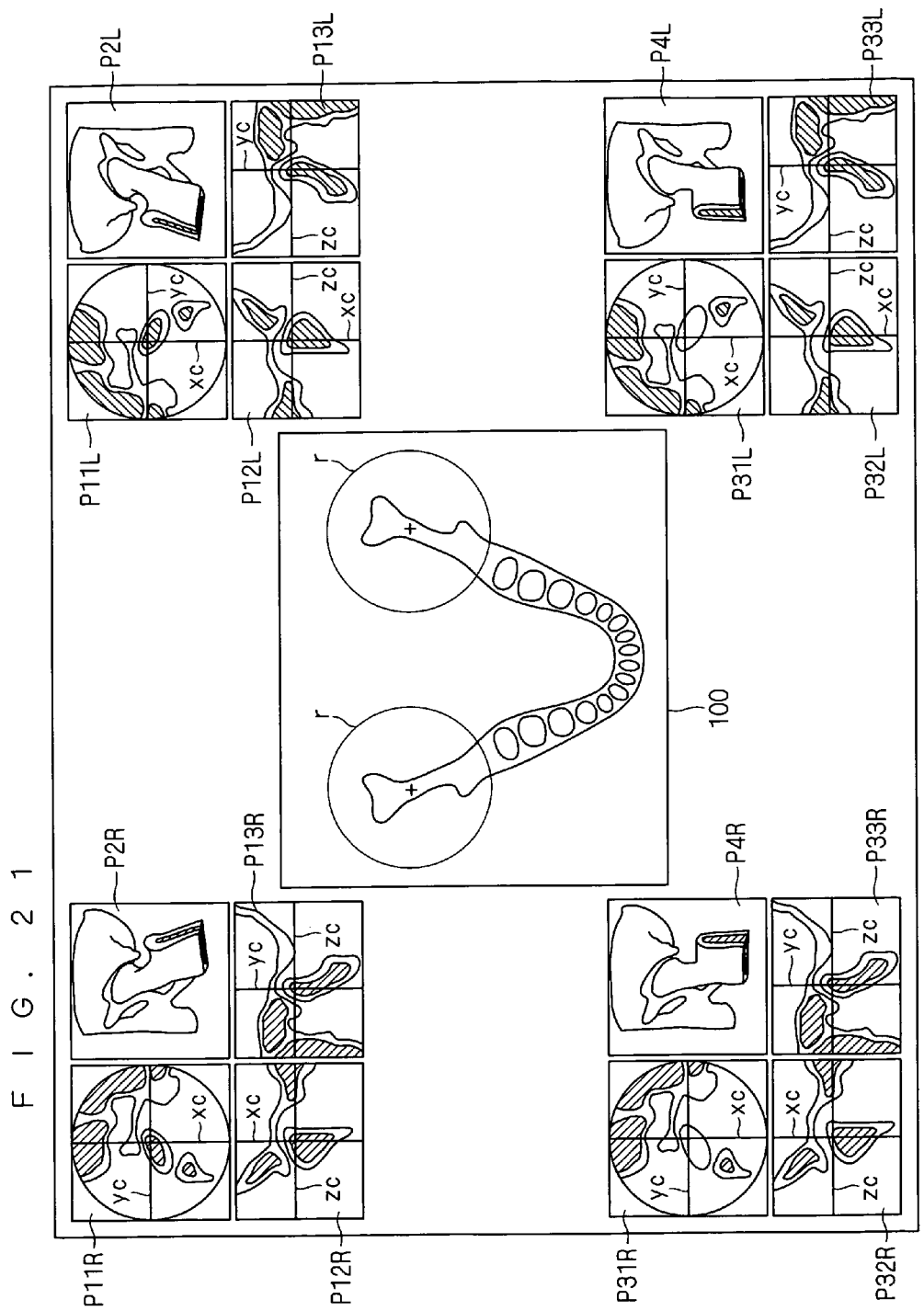

Further, in FIG. 21, shown is an exemplary case where the illustration 100 of the dental arch including the temporomandibular joints and the CT images of the temporomandibular joints in the closed and open states are displayed. In FIG. 21, the illustration 100 is displayed in the center and the CT images of the temporomandibular joints in the closed state are displayed on the upper stage and the CT images of the temporomandibular joints in the open state are displayed on the lower stage. Among the CT images on the upper stage of FIG. 21, the cross sectional CT images P11R to P13R of the right-side temporomandibular joint in the closed state and the volume rendering image P2R of the right-side temporomandibular joint are displayed on the left side of the screen, and the cross sectional CT images P11L to P13L of the left-side temporomandibular joint in the closed state and the volume rendering image P2L of the left-side temporomandibular joint are displayed on the right side of the screen. Among the CT images on the lower stage of FIG. 21, the cross sectional CT images P31R to P33R of the right-side temporomandibular joint in the open state and the volume rendering image P4R of the right-side temporomandibular joint are displayed on the left side of the screen, and the cross sectional CT images P31L to P33L of the left-side temporomandibular joint in the open state and the volume rendering image P4L of the left-side temporomandibular joint are displayed on the right side of the screen.

Thus, also by displaying the illustration 100 and the CT images of the temporomandibular joints in the closed and open states for comparison, it is possible to examine the closed and open states of the temporomandibular joints while recognizing the positions of the temporomandibular joints in the illustration 100 and therefore possible to support efficient diagnoses and effective explanations for patients.

Figure 22:
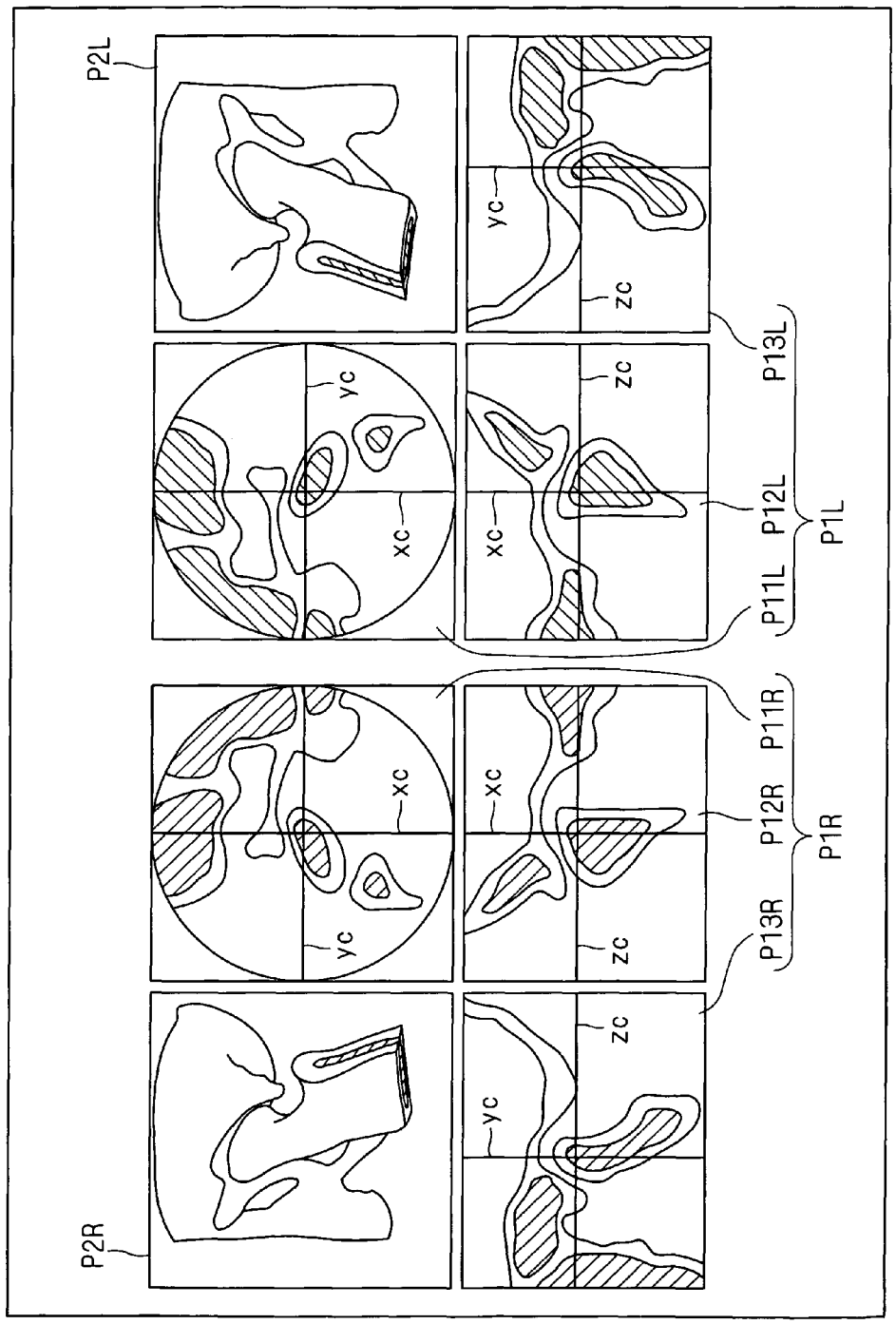

In FIG. 22, shown is an exemplary case where the CT images of the temporomandibular joints in the closed state are displayed in an arrangement different from that of FIG. 16. In FIG. 22, like in FIG. 16, the cross sectional CT image P1R of the right-side temporomandibular joint in the closed state and the volume rendering image P2R of the right-side temporomandibular joint are displayed on the left side of the screen, and the cross sectional CT image P1L of the left-side temporomandibular joint in the closed state and the volume rendering image P2L of the left-side temporomandibular joint are displayed on the right side of the screen. In FIG. 22, however, unlike in FIG. 16, the volume rendering image P2R of the right-side temporomandibular joint is displayed in the upper left, the cross sectional CT image P11R of the right-side temporomandibular joint sectioned by the xy plane is displayed in the upper right, the cross sectional CT image P12R of the right-side temporomandibular joint sectioned by the xz plane is displayed in the lower right, and the cross sectional CT image P13R of the right-side temporomandibular joint sectioned by the yz plane is displayed in the lower left. The arrangement of the cross sectional CT image P1L of the left-side temporomandibular joint in the closed state and the volume rendering image P2L of the left-side temporomandibular joint is the same as that of FIG. 16.

By displaying the CT images of the right-side temporomandibular joint and the cross sectional CT images of the left-side temporomandibular joint in mirror symmetry, the images can be displayed in a form close to the actual arrangement of the temporomandibular joints, and it is therefore possible to support efficient diagnoses and effective explanations for patients.

Figure 23:
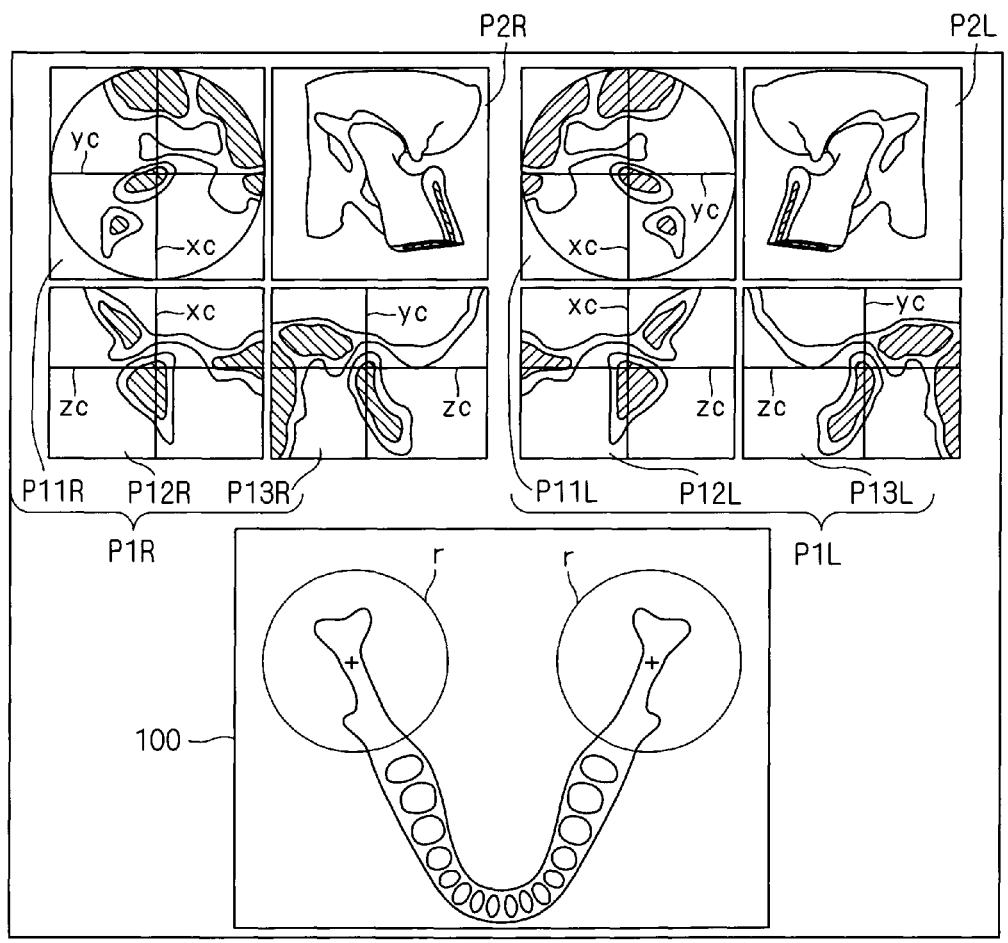
Figure 24:
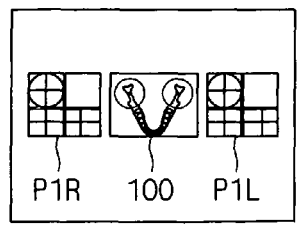

In FIG. 23, unlike in FIG. 21, the illustration 100 of the dental arch including the temporomandibular joints and the CT images of the temporomandibular joints in the closed state. In FIG. 23, the cross sectional CT images P11R to P13R of the right-side temporomandibular joint in the closed state and the volume rendering image P2R of the right-side temporomandibular joint are displayed on the left side of the upper stage of the screen, and the cross sectional CT images P11L to P13L of the left-side temporomandibular joint in the closed state and the volume rendering image P2L of the left-side temporomandibular joint are displayed on the right side of the upper stage of the screen. Further, in FIG. 23, the illustration 100 of the dental arch including the temporomandibular joints is displayed on the lower stage of the screen. The CT images of the temporomandibular joints in the closed state may be displayed in the same layout, instead of the CT images of the temporomandibular joints in the open state. The display manner of the illustration 100 of the dental arch including the temporomandibular joints and the CT images of the temporomandibular joints in the closed state is not limited to that of FIG. 23 but the illustration 100 and the CT images of the temporomandibular joints in the closed state may be displayed in a row as shown in FIG. 24.

Thus, by displaying the illustration 100 of the dental arch including the temporomandibular joints, and the CT images of the temporomandibular joints in the closed state, it is possible to take a view of the whole and therefore possible to support efficient diagnoses and effective explanations for patients.

Figure 25:
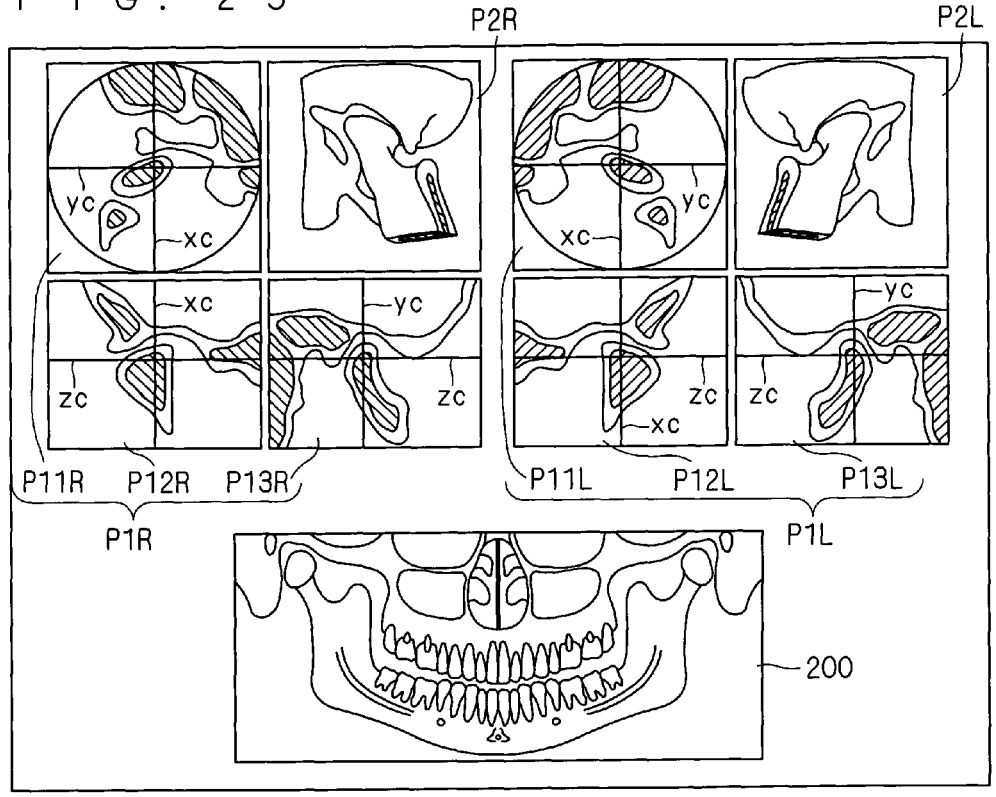
Figure 26:
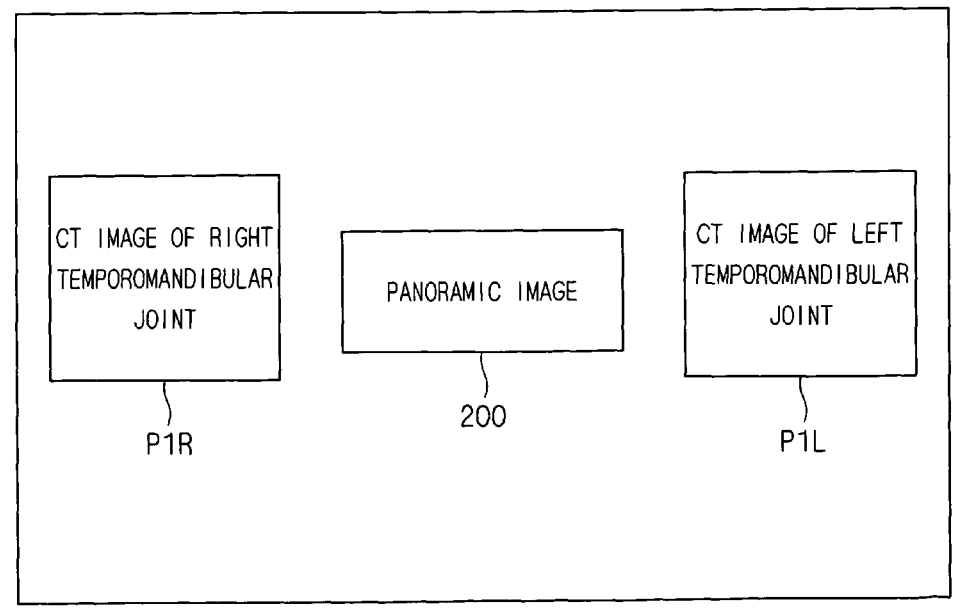

In FIG. 25, unlike in FIG. 20, the panoramic image 200 and the CT images of the temporomandibular joints in the closed state. In FIG. 25, the cross sectional CT images P11R to P13R of the right-side temporomandibular joint in the closed state and the volume rendering image P2R of the right-side temporomandibular joint are displayed on the left side of the upper stage of the screen, and the cross sectional CT images P11L to P13L of the left-side temporomandibular joint in the closed state and the volume rendering image P2L of the left-side temporomandibular joint are displayed on the right side of the upper stage of the screen. Further, in FIG. 25, the panoramic image 200 is displayed on the lower stage of the screen. The CT images of the temporomandibular joints in the closed state may be displayed in the same layout, instead of the CT images of the temporomandibular joints in the open state. The display manner of the panoramic image 200 and the CT images of the temporomandibular joints in the closed state is not limited to that of FIG. 25 but the panoramic image 200 and the CT images of the temporomandibular joints in the closed state may be displayed in a row as shown in FIG. 26.

Thus, by displaying the panoramic image 200 and the CT images of the temporomandibular joints in the closed state, it is possible to take a view of the whole and therefore possible to support efficient diagnoses and effective explanations for patients.

The above examples relate to the temporomandibular joints and discussion has been made on the CT images of the living organs symmetrically located with respect to a plane including the median line. The present invention, however, is not limited to the above case but CT images of the living organs which are vertically symmetrical with respect to a predetermined plane, such as an upper tooth row and a lower tooth row which are vertically symmetrical with respect to an occlusal surface, may be displayed.

Figure 27:
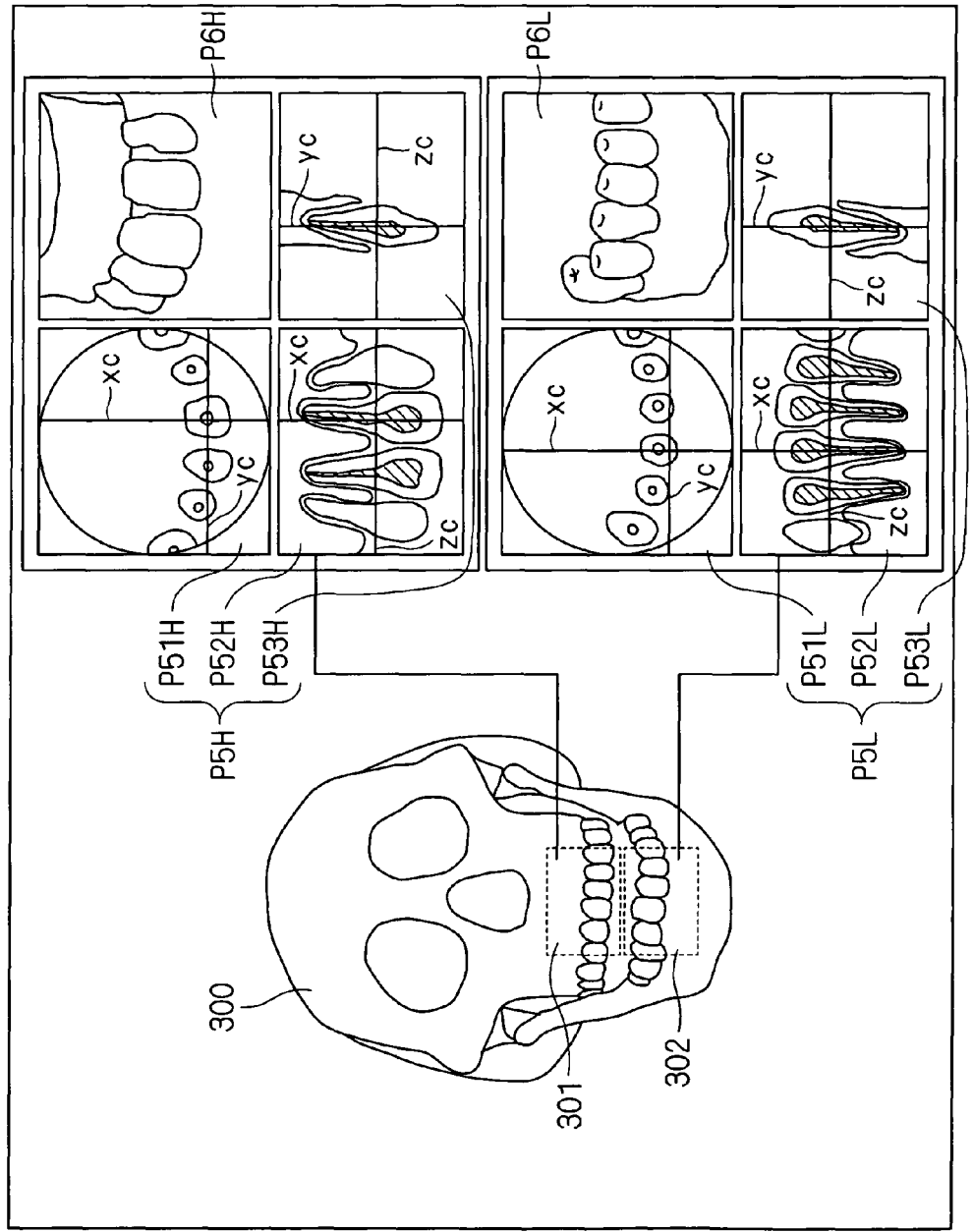

Now, discussion will be made on the medical X-ray CT imaging apparatus M which performs CT imaging on an upper tooth row and a lower tooth row. The medical X-ray CT imaging apparatus M uses an illustration 300 of a skull shown on the left side of FIG. 27 to specify an upper tooth row 301 and a lower tooth row 302 which are imaging regions r and moves the X-ray generation part 10 and the X-ray detection part 20 on the basis of the specified positions to perform CT imaging. The apparatus M reconstructs CT images on the basis of the data captured by the CT imaging and displays the CT images shown on the left side of FIG. 27 on the display part 88. In FIG. 27, the illustration 300 is displayed on the right side of the screen, and a CT image P5H of the upper tooth row 301 and a volume rendering image P6H of the upper tooth row 301 are displayed on the upper left of the screen, and a CT image P5L of the lower tooth row 302 and a volume rendering image P6L of the lower tooth row 302 are displayed on the lower left of the screen.

The CT image P5H includes a cross sectional CT image P51H of the upper tooth row 301 sectioned by the xy plane which is shown in the upper left, a cross sectional CT image P52H of the upper tooth row 301 sectioned by the xz plane which is shown in the lower left, and a cross sectional CT image P53H of the upper tooth row 301 sectioned by the yz plane which is shown in the lower right. The CT image P5L includes a cross sectional CT image P51L of the lower tooth row 302 sectioned by the xy plane which is shown in the upper left, a cross sectional CT image P52L of the lower tooth row 302 sectioned by the xz plane which is shown in the lower left, and a cross sectional CT image P53L of the lower tooth row 302 sectioned by the yz plane which is shown in the lower right. Though an actual occlusion has a deviation between the upper tooth row and the lower tooth row, the positions of the displayed cross sectional CT images P53H and P53L are adjusted so that these cross sectional CT images may be on the same y axis. Though the illustration 300 and the CT images of the upper tooth row and the lower tooth row are displayed in FIG. 27, the present invention is not limited to this but there may be a case where only the CT images of the upper tooth row and the lower tooth row are displayed.

It is desired to control the cone beam for the CT imaging to be emitted to only the imaging target portion, and there is a possible configuration to control the vertical length of the cone beam to cover only one of the teeth of the upper jaw and those of the lower jaw. In this case, if the imaging target portion changes vertically, it is necessary to somehow adjust the position of the radiation field of the cone beam to the position of the imaging target portion.

Figure 28:
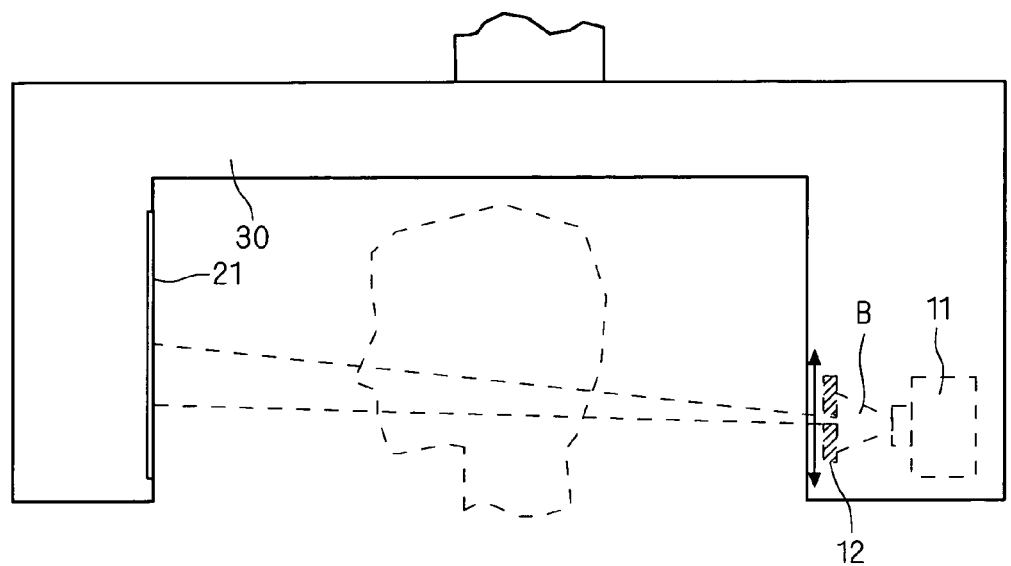
Figure 29:
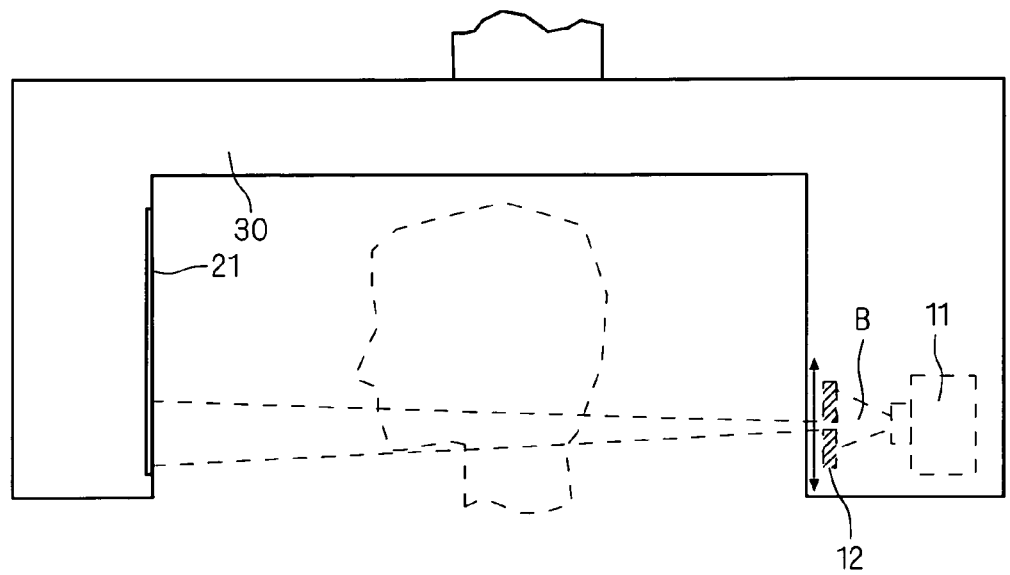

In the exemplary configurations of FIGS. 5 and 6, specifically, the supporting part 30 may be moved up and down relative to the subject holding part 40, the subject holding part 40 may be moved up and down relative to the supporting part 30, or both the parts may be moved up and down mutually. As shown in the exemplary configurations of FIGS. 8 and 9, the Z-axis motor 60z may be driven to move the subject holding part 40 up and down relative to the supporting part 30. As shown in the exemplary configurations of FIGS. 28 and 29, the radiation field control part 12 placed in front of the X-ray generator 11 may be moved up and down by a well-known and not-shown actuator using a motor or the like in a direction indicated by the arrow of the figures, to thereby control the cone beam to be projected upward or downward. FIG. 28 shows a case of irradiating the teeth of the upper jaw and FIG. 29 shows a case of irradiating the teeth of the lower jaw.

Figure 30:
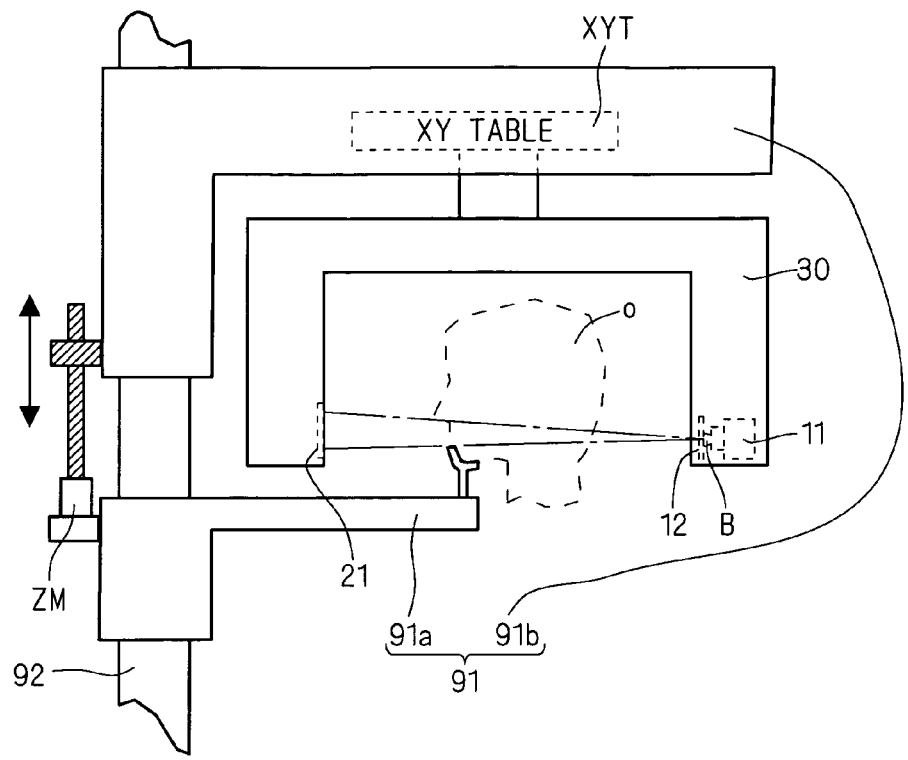

Further, as shown in FIG. 30, there may be a configuration wherein the up-and-down moving frame 91 includes an up-and-down moving frame lower part 91a provided with a chin rest on which the chin of a patient o as the subject is placed in order for the head to be held and an up-and-down moving frame upper part 91b which moves up and down relative to the up-and-down moving frame lower part 91a and the whole of the up-and-down moving frame lower part 91a and the up-and-down moving frame upper part 91b is moved relative to the column 92 by a not-shown moving mechanism, to be thereby vertically positioned in accordance with the physique of the patient o, and then the up-and-down moving frame upper part 91b can move up and down relative to the up-and-down moving frame lower part 91a, to be adjusted to the target portion of the CT imaging.

In the exemplary configuration of FIG. 30, the up-and-down moving frame lower part 91a is provided with an up-and-down movement driving motor ZM including a thread axis having a longitudinal axis in the direction of vertical movement of the up-and-down moving frame upper part 91b, part of the up-and-down moving frame upper part 91b serves as an internal thread to be in threaded engagement with the thread axis, and the up-and-down moving frame upper part 91b can be moved up and down relative to the up-and-down moving frame lower part 91b by the drive of the up-and-down movement driving motor ZM.

Figure 31:
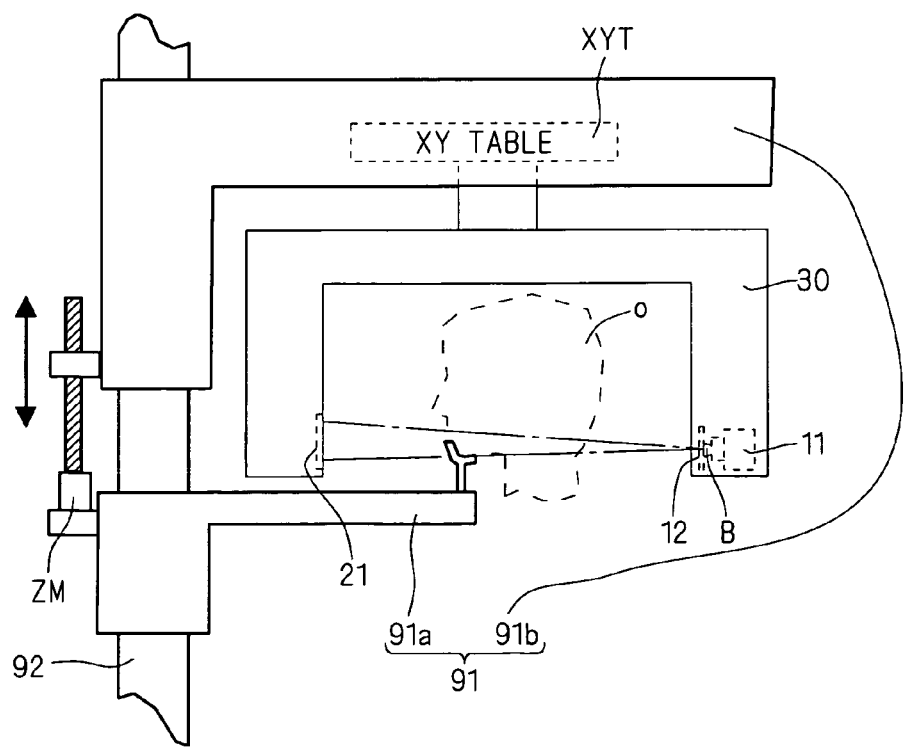

FIG. 30 shows a case of irradiating the teeth of the upper jaw, and FIG. 31 shows a case of irradiating the teeth of the lower jaw.

Further, as shown in FIG. 32, there may be a case where an XY table XYT having the same table as the X table 35X and the Y table 35Y shown in FIG. 2, which axially supports the supporting part 30, and a Z table ZT for moving the XY table XYT up and down are provided inside the up-and-down moving frame 91 and the supporting part 30 is moved up and down relative to the subject o or the subject holding part 40, whereby the radiation field of the cone beam is controlled to be directed upward or downward. FIG. 32 shows a case of irradiating the teeth of the upper jaw.

The case of irradiating the teeth of the lower jaw is almost the same as the cases shown in FIGS. 29 and 31 and will not therefore be shown.

In FIGS. 28 to 32, the constituent elements common to those of FIGS. 1 to 9 are represented by the same reference signs and detailed description thereof will be omitted.

Figure 33:
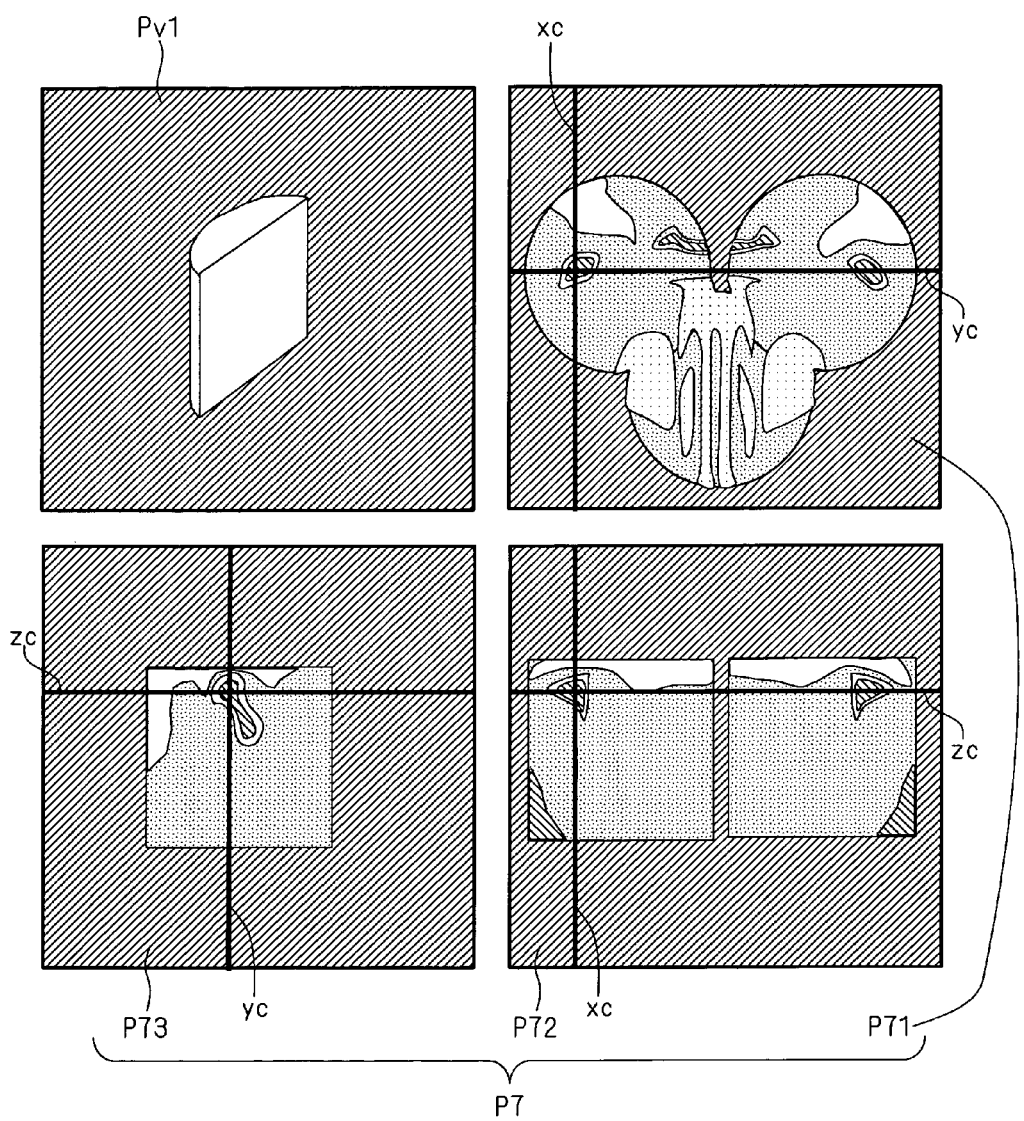
FIG. 33 is a view showing an example of image display in a case where serial CT imaging is performed on a first living organ, a second living organ, and a third living organ.

FIG. 33 shows an example of image display in a case where serial CT imaging is performed on the first living organ, the second living organ, and the third living organ such as the right living organ or, the left living organ ol, and the central living organ oc discussed earlier with reference to FIG. 18.

The CT imaging data obtained by the CT imaging on the first living organ is defined as first living organ CT imaging data io1, the CT imaging data obtained by the CT imaging on the second living organ is defined as second living organ CT imaging data io2, and the CT imaging data obtained by the CT imaging on the third living organ is defined as third living organ CT imaging data io3.

The image operation part 84 performs position calculation on the first living organ CT imaging data io1, the second living organ CT imaging data io2, and the third living organ CT imaging data io3 so that actual positions of the first living organ, the second living organ, and the third living organ in the living body can be reflected with fidelity, to thereby synthesize one CT imaging data ios.

The position calculation in synthesis may be performed, for example, by measuring the positions of the imaging region rr, the imaging region rl, and the imaging region rc from the amount of movement of the rotation arm during the serial CT imaging of the first living organ, the second living organ, and the third living organ and reflecting the positions of the imaging region rr, the imaging region rl, and the imaging region rc on the arrangement of the first living organ CT imaging data io1, the second living organ CT imaging data io2, and the third living organ CT imaging data io3 with fidelity in the synthesizing operation.

Figure 34:
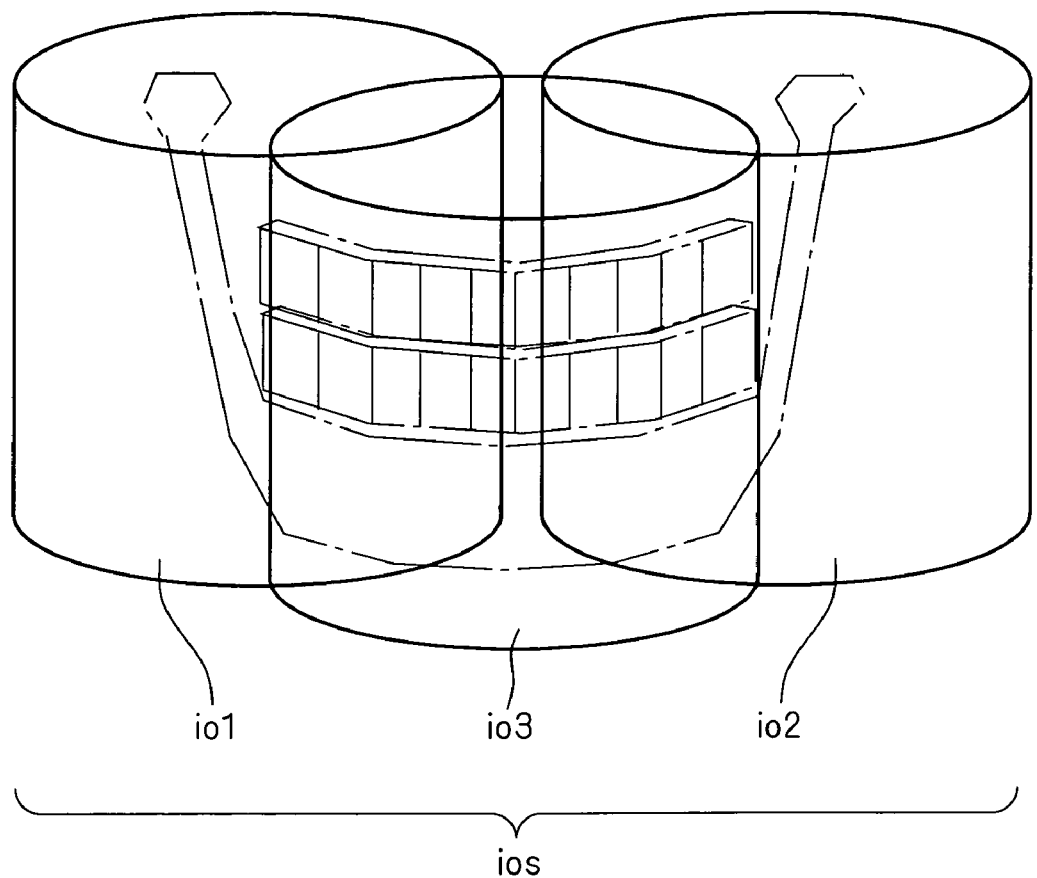
FIG. 34 is a view schematically showing synthesized CT imaging data ios.

Though the actual CT imaging data is not visible data until being reconstructed and displayed, the synthesized CT imaging data ios is schematically shown in FIG. 34.

P71, P72, and P73 in FIG. 33 show CT images obtained by reconstructing the synthesized CT imaging data ios.

The cross sectional CT image P7 includes the cross sectional CT image P71 of the left and right temporomandibular joints sectioned by the xy plane which is shown in the upper right, the cross sectional CT image P72 of the left and right temporomandibular joints sectioned by the xz plane which is shown in the lower right, and the cross sectional CT image P73 of the left-side temporomandibular joint sectioned by the yz plane which is shown in the lower left, and these cross sectional CT images are displayed. Like in FIG. 16 and the like, the x cursor xc, the y cursor yc, and the z cursor zc are also displayed.

In the upper left, a volume rendering image Pv1 showing only the left-side temporomandibular joint is also displayed. Since the volume rendering image Pv1 is shown in FIG. 16 and other figures, the image is represented by a simplified shape in FIG. 33.

Figure 35:
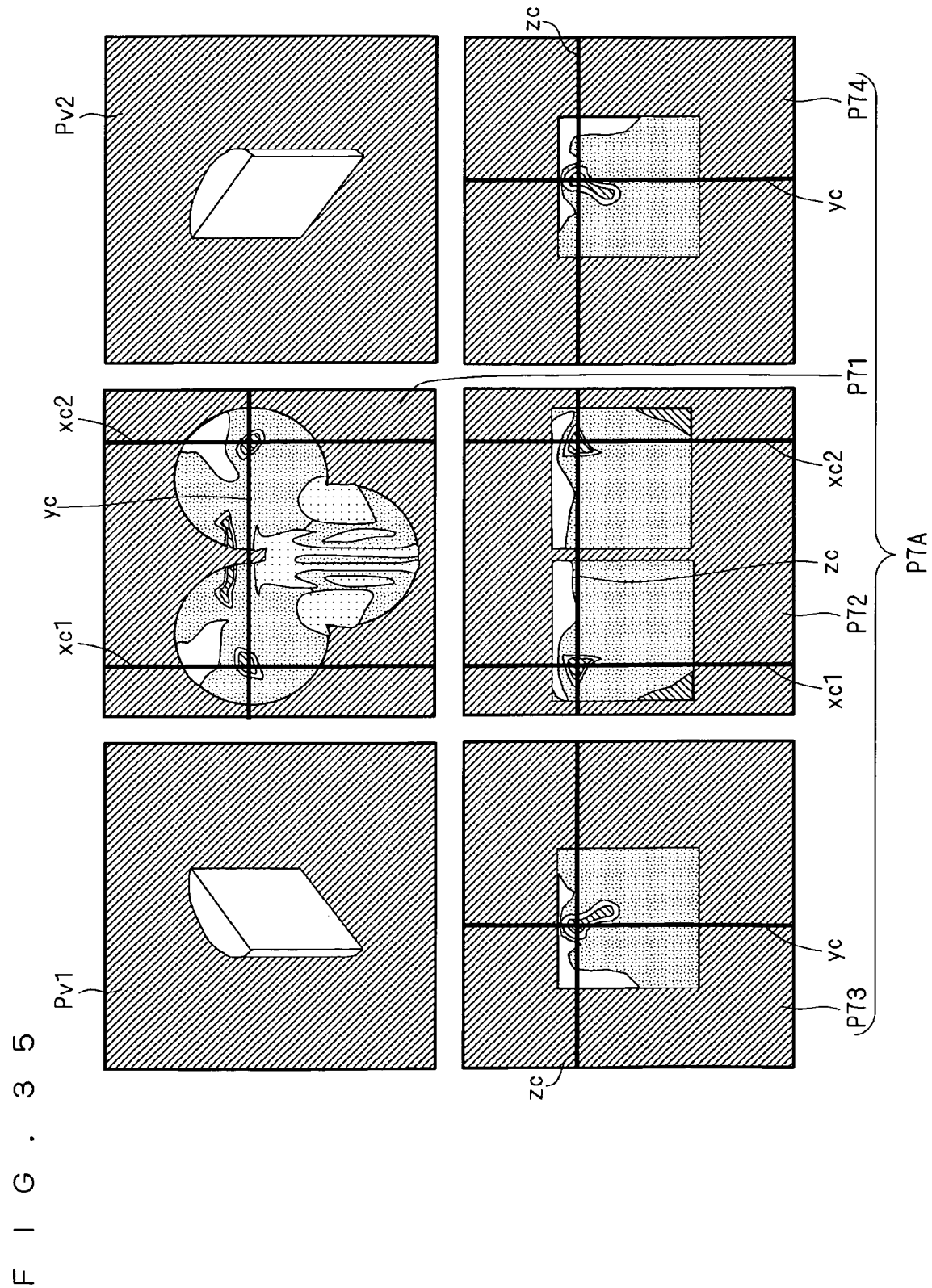
FIGS. 35 and 36 are views showing another example of image display in the case where the serial CT imaging is performed on the first living organ, the second living organ, and the third living organ.

FIG. 35 shows an exemplary display where the CT image of FIG. 34 is further developed.

The display of FIG. 35 is basically the same as that of FIG. 34 but different therefrom in that two x cursors xc1 and xc2 indicating the positions of two yz planes of which the positions are different, a cross sectional CT image P74 showing a section cut by another yz plane, and a volume rendering image Pv2 showing only the right-side temporomandibular joint are also displayed.

A cross sectional CT image P7A includes the cross sectional CT image P71, the cross sectional CT image P72, the cross sectional CT image P73, and the cross sectional CT image P74.

As a matter of course, both the x cursors xc1 and xc2 can be moved and both the yz plane shown in P73 and the yz plane shown in P74 can be changed.

Such a display allows, the first living organ and the second living organ to be displayed for comparison, and it is therefore possible to perform more effective diagnoses.

Though FIG. 34 shows the exemplary image display of the synthesized image obtained by combining the CT imaging data of the third living organ with the CT imaging data of the first living organ and the second living organ when the serial CT imaging is performed on the first living organ, the second living organ, and the third living organ, the generation of the CT imaging data by performing position calculation so that actual positions of the organs in the living body can be reflected with fidelity may be performed only on the first living organ and the second living organ.

Figure 19:
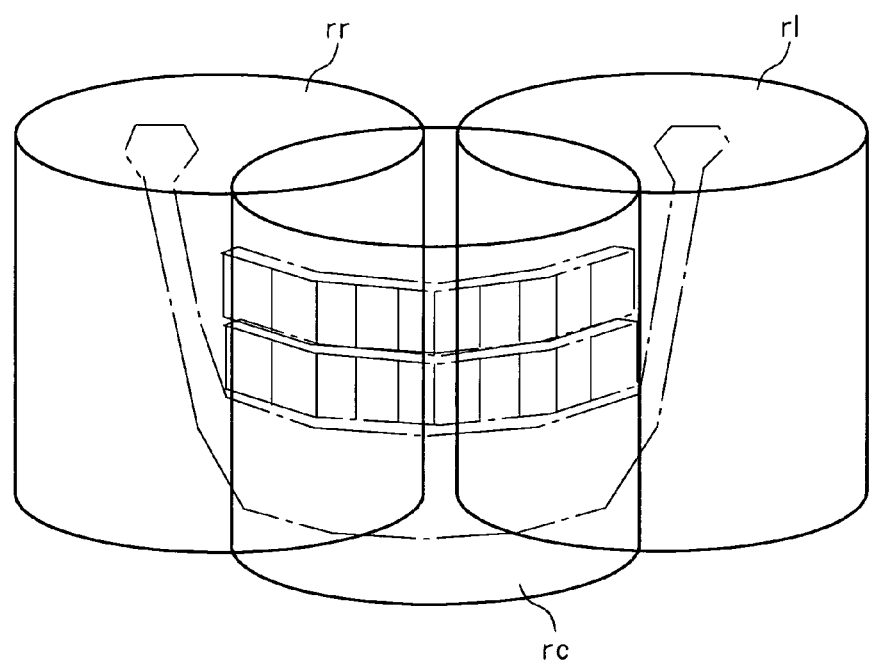
Figure 36:
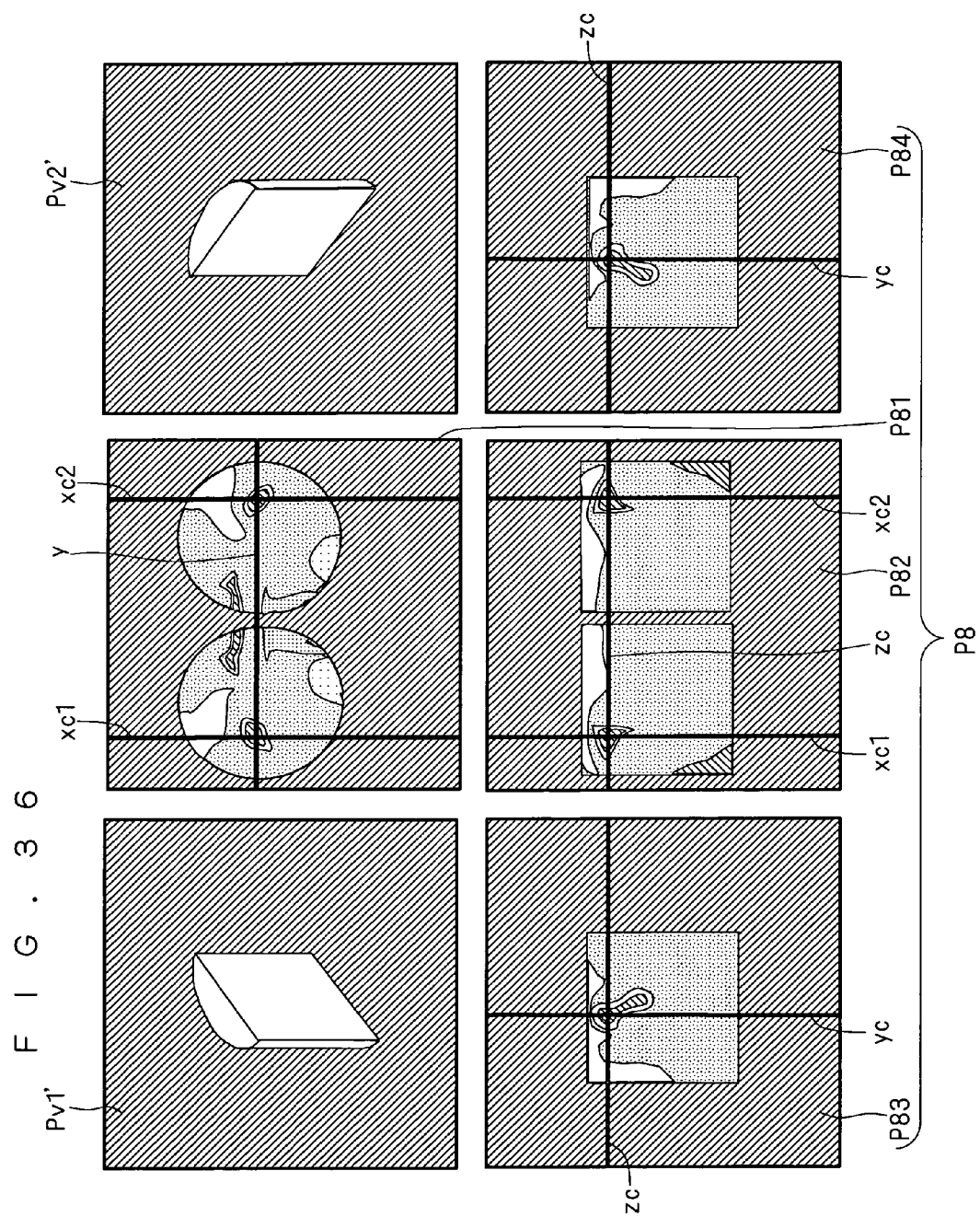

FIG. 36 shows an exemplary display of the reconstructed CT imaging data, where the image operation part 84 performs position calculation on the first living organ CT imaging data io1 and the second living organ CT imaging data io2 described with reference to FIG. 19 so that actual positions of the first living organ and the second living organ in the living body can be reflected with fidelity, to thereby synthesize one CT imaging data ios' which is not shown, and the CT imaging data is reconstructed.

There may be a case where the serial CT imaging is performed, as discussed with reference to FIG. 18, on the first living organ, the second living organ, and the third living organ such as the right living organ or, the left living organ ol, and the central living organ oc discussed earlier and only the CT imaging data of the first living organ and the second living organ are combined to be displayed, with the CT imaging data of the third living organ excluded from the data to be combined, or there may be another case where the imaging is performed only on the first living organ and the second living organ and then the CT imaging data of the first living organ and the second living organ are combined to be displayed.

In the case where the imaging is performed only on the first living organ and the second living organ and then the CT imaging data of the first living organ and the second living organ are combined, the operation therefor is as follows.

Assuming that the right-side temporomandibular joint and the portions in the vicinity thereof are defined as the right-side living organ or and the left-side temporomandibular joint and the portions in the vicinity thereof are defined as the left-side living organ ol, the right-side imaging region rr for the CT imaging of the right-side living organ or and the left-side imaging region rl for the CT imaging of the left-side living organ ol are set.

The CT imaging is performed consecutively on the imaging region rr and the imaging region rl, but as to the sequence of imaging, any one of these may be first. Herein, it is assumed that one of the right-side living organ or and the left-side living organ ol is defined as the first living organ. The imaging region rr and the imaging region rl may be specified by the operator using the imaging region specifying part 83 as discussed earlier or may be positionally set in advance with respect to the position of the subject holding part with the dental arch of a standard skeleton obtained statistically as a reference.

Hereinafter, the synthesis and display of the CT imaging data are common to the case where the serial CT imaging is performed on the first living organ, the second living organ, and the third living organ and only the CT imaging data of the first living organ and the second living organ are combined to be displayed, with the CT imaging data of the third living organ excluded from the data to be combined, and the case where the imaging is performed only on the first living organ and the second living organ and then the CT imaging data of the first living organ and the second living organ are combined to be displayed.

The CT imaging data obtained by the CT imaging on the first living organ is defined as first living organ CT imaging data io1, and the CT imaging data obtained by the CT imaging on the second living organ is defined as second living organ CT imaging data io2.

The image operation part 84 performs position calculation on the first living organ CT imaging data io1 and the second living organ CT imaging data io2 so that actual positions of the first living organ and the second living organ in the living body can be reflected with fidelity, to thereby synthesize one CT imaging data ios'.

The position calculation in synthesis may be performed, for example, by measuring the positions of the imaging region rr and the imaging region rl from the amount of movement of the rotation arm during the serial CT imaging of the first living organ and the second living organ and reflecting the positions of the imaging region rr and the imaging region rl on the arrangement of the first living organ CT imaging data io1 and the second living organ CT imaging data io2 with fidelity in the synthesizing operation.

P81, P82, P83, P84 and Pv in FIG. 36 show CT images obtained by reconstructing the synthesized CT imaging data ios.

The cross sectional CT image P8 includes the cross sectional CT image P81 of the left and right temporomandibular joints sectioned by the xy plane which is shown in the upper right, the cross sectional CT image P82 of the left and right temporomandibular joints sectioned by the xz plane which is shown in the lower right, the cross sectional CT image P83 of the left-side temporomandibular joint sectioned by the yz plane which is shown in the lower left, and the cross sectional CT image P84 of the right-side temporomandibular joint sectioned by the yz plane which is shown in the lower right, and these cross sectional CT images are displayed.

A volume rendering image Pv1' showing only the left-side temporomandibular joint is displayed in the upper left, and a volume rendering image Pv2' showing only the right-side temporomandibular joint is displayed in the upper right.

The x cursor xc, the y cursor yc, and the z cursor zc are also displayed like in FIG. 16 and other figures, but the two x cursors xc1 and xc2 indicating the positions of the two yz planes of which the positions are different are displayed unlike FIG. 16 and other figures.

As a matter of course, both the x cursors xc1 and xc2 can be moved and both the yz plane shown in P83 and the yz plane shown in P84 can be changed.

Since the volume rendering images Pv1' and Pv2' are shown in FIG. 16 and other figures, the images are represented by simplified shapes in FIG. 36.

Such a display allows the first living organ and the second living organ to be displayed for comparison, and it is therefore possible to perform more effective diagnoses.

Thus, the medical X-ray CT imaging apparatus M of the present invention can be applied to any living organs symmetrically located with respect to a predetermined plane.

The invention claimed is:
1. A medical X-ray CT imaging apparatus comprising:
an X-ray source for generating a cone beam;
an X-ray detection part for detecting said cone beam;
a supporting part for arranging said X-ray source and said X-ray detection part to be opposed to each other with a subject interposed therebetween;
a subject holding part for holding said subject;
a rotation driving part for driving said supporting part and said subject holding part to rotate relative to each other;
an axis moving part for causing the rotation axis of said rotation driving part to be movable relative to said subject;

a control part for automatically and consecutively performing X-ray CT imaging of respective imaging regions specified for a first living organ and a second living organ which are symmetrically located with respect to a plane parallel or perpendicular to a median line of said subject by using said axis moving part and said rotation driving part, in a manner of imaging said first living organ and thereafter moving the rotation axis of the rotation driving part relative to said subject and imaging said second living organ;

an image processing part for reconstructing respective CT images of said first living organ and said second living organ on the basis of an electrical signal which are obtained by said X-ray detection part through said X-ray CT imaging; and a display part for displaying said CT images of said first living organ and said second living organ which are obtained by said image processing part.

2. The medical X-ray CT imaging apparatus according to claim 1, further comprising an imaging region specifying part for specifying respective imaging regions for said first living organ and said second living organ.

3. The medical X-ray CT imaging apparatus according to claim 1, wherein

X-ray CT imaging of a third living organ located between said first living organ and said second living organ is performed, and said X-ray CT imaging of said third living organ is automatically performed consecutively before or after said X-ray CT imaging of said first living organ and said second living organ or between said X-ray CT imaging of said first living organ and said X-ray CT imaging of said second living organ.

4. The medical X-ray CT imaging apparatus according to claim 1, wherein said rotation driving part and said axis moving part perform panoramic radiography in conjunction with the movement of said rotation axis.

5. The medical X-ray CT imaging apparatus according to claim 1, further comprising a storage part for storing said CT image of said first living organ and said CT image of said second living organ which are captured consecutively by said X-ray CT imaging while associating said CT images with each other.

6. The medical X-ray CT imaging apparatus according to claim 2, wherein said imaging region specifying part displays an illustration including at least said first living organ and said second living organ on said display part, to specify said imaging regions on the basis of said illustration.

7. The medical X-ray CT imaging apparatus according to claim 1, further comprising an imaging condition changing part for selecting whether said subject is an adult or a child and changing the condition for said X-ray CT imaging according to the selection.

8. The medical X-ray CT imaging apparatus according to claim 1, wherein said first living organ and said second living organ are temporomandibular joints or otolaryngological regions.

9. A medical X-ray CT imaging apparatus comprising:
an X-ray source for generating a cone beam;
an X-ray detection part for detecting said cone beam;
a supporting part for arranging said X-ray source and said X-ray detection part to be opposed to each other with a subject interposed therebetween;
a subject holding part for holding said subject;
a rotation driving part for driving said supporting part and said subject holding part to rotate relative to each other;
an axis moving part for causing the rotation axis of said rotation driving part to be movable relative to said subject;
a control part for automatically and consecutively performing X-ray CT imaging of respective imaging regions specified for a first living organ and a second living organ which are symmetrically located with respect to a predetermined plane by using said axis moving part and said rotation driving part;
an image processing part for reconstructing respective CT images of said first living organ and said second living organ on the basis of an electrical signal which are obtained by said X-ray detection part through said X-ray CT imaging; and
a display part for displaying said CT images of said first living organ and said second living organ which are obtained by said image processing part, wherein
said first living organ and said second living organ are temporomandibular joints, and
said X-ray CT imaging of said temporomandibular joints is performed consecutively on either one of open and closed states thereof and then on the other state.

10. The medical X-ray CT imaging apparatus according to claim 9, wherein said display part displays said CT images of said first living organ and said second living organ in said open state and said CT images of these living organs in said closed state on one display screen for comparison.

11. The medical X-ray CT imaging apparatus according to claim 9, wherein said CT images of said temporomandibular joints captured by said X-ray CT imaging, from said open state to said closed state, are displayed on said display part as a moving image.

12. The medical X-ray CT imaging apparatus according to claim 1, wherein said display part displays said CT images of said first living organ and said second living organ on one display screen for comparison.

13. The medical X-ray CT imaging apparatus according to claim 2, wherein at least one of said X-ray source and said axis moving part is adjusted on the basis of the sizes of said first living organ and said second living organ specified by said imaging region specifying part.

14. The medical X-ray CT imaging apparatus according to claim 1, wherein said display part displays a CT image obtained by combining CT imaging data of said first living organ and said second living organ and arranging said CT imaging data in accordance with the actual three-dimensional positions of said first living organ and said second living organ.

15. The medical X-ray CT imaging apparatus according to claim 3, wherein said display part displays a CT image obtained by combining CT imaging data of said first living organ, said second living organ, and said third living organ and arranging said CT imaging data in accordance with the actual three-dimensional positions of said first living organ, said second living organ, and said third living organ.

* * * * *